(12) United States Patent
Hejazi et al.

(10) Patent No.: US 12,708,145 B2
(45) Date of Patent: Aug. 18, 2026

(54) AEROSOL DELIVERY DEVICE WITH SEGMENTED ELECTRICAL HEATER

(71) Applicant: RAI Strategic Holdings, Inc., Winston-Salem, NC (US)

(72) Inventors: Vahid Hejazi, Concord, NC (US); Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

(21) Appl. No.: 18/402,005

(22) Filed: Jan. 2, 2024

(65) Prior Publication Data

US 2024/0148063 A1 May 9, 2024

Related U.S. Application Data

(63) Continuation of application No. 17/165,188, filed on Feb. 2, 2021, now Pat. No. 11,896,053, which is a continuation of application No. 16/110,223, filed on Aug. 23, 2018, now Pat. No. 10,939,707.

(51) Int. Cl.

*A24F 40/46* (2020.01)
*A24B 15/167* (2020.01)
*A24F 40/20* (2020.01)
*A24F 40/42* (2020.01)

(Continued)

(52) U.S. Cl.

CPC ............ *A24F 40/46* (2020.01); *A24B 15/167* (2016.11); *A24F 40/42* (2020.01); *A61M 11/042* (2014.02); *A61M 15/06* (2013.01); *A24F 40/20* (2020.01); *A61M 2205/3653* (2013.01)

(58) Field of Classification Search

None

See application file for complete search history.

(56) References Cited

U.S. PATENT DOCUMENTS 2,057,353 A 10/1936 Whittemore, Jr.
2,104,266 A 1/1938 McCormick
3,200,819 A 8/1965 Gilbert (Continued)

FOREIGN PATENT DOCUMENTS

CL 199400288 11/1995
CL 199600626 5/1996

(Continued)

OTHER PUBLICATIONS

International Search Report from corresponding International Appl. No. PCT/IB2019/057092, dated Dec. 20, 2019.

*Primary Examiner* — Thor S Campbell

(74) *Attorney, Agent, or Firm* — Womble Bond Dickinson (US) LLP

(57) ABSTRACT

The present disclosure provides an aerosol delivery device. In various implementations, the aerosol delivery device comprises a control body having an outer housing, an electrical energy source located within the housing, a control component operatively connected to the electrical energy source, a heating assembly operatively connected to the control component, and an aerosol source member that includes an aerosol generating component configured to be positioned proximate the heating assembly. The heating assembly comprises a series of heating members, and each heating member is independent and distinct and configured to heat a segment of the aerosol source member.

13 Claims, 12 Drawing Sheets

(51) Int. Cl.
*A61M 11/04* (2006.01)
*A61M 15/06* (2006.01)

(56) References Cited

U.S. PATENT DOCUMENTS 4,922,901 A 5/1990 Brooks et al.
5,060,671 A * 10/1991 Counts .................... A24F 40/50 131/273
5,093,894 A * 3/1992 Deevi ..................... A24F 40/46 392/404
5,261,424 A 11/1993 Sprinkel, Jr.
5,388,574 A 2/1995 Ingebrethsen et al.
5,530,225 A * 6/1996 Hajaligol ................ A24F 40/46 131/194
5,687,746 A 11/1997 Rose et al.
5,726,421 A 3/1998 Fleischhauer et al.
5,865,185 A * 2/1999 Collins .................... H05B 3/24 131/194
5,894,841 A 4/1999 Voges
6,125,853 A 10/2000 Susa et al.
6,155,268 A 12/2000 Takeuchi
7,117,867 B2 * 10/2006 Cox ........................ A24F 40/60 128/200.14
7,832,410 B2 11/2010 Hon
8,314,591 B2 11/2012 Terry et al.
8,365,742 B2 2/2013 Hon
8,499,766 B1 8/2013 Newton
2005/0016550 A1 1/2005 Katase
2006/0196518 A1 9/2006 Hon
2008/0092912 A1 4/2008 Robinson et al.
2009/0095311 A1 4/2009 Hon
2009/0126745 A1 5/2009 Hon
2009/0188490 A1 7/2009 Hon
2009/0272379 A1 11/2009 Thorens et al.
2011/0094523 A1 4/2011 Thorens et al.
2011/0126848 A1 * 6/2011 Zuber ..................... A24F 40/46 131/329
2011/0155718 A1 6/2011 Greim et al.
2011/0168194 A1 7/2011 Hon
2011/0265806 A1 11/2011 Alarcon et al.
2011/0290248 A1 12/2011 Schennum
2012/0111347 A1 5/2012 Hon
2012/0260927 A1 * 10/2012 Liu ......................... A24F 40/46 219/525
2012/0279512 A1 11/2012 Hon
2013/0037041 A1 2/2013 Worm et al.
2013/0056013 A1 3/2013 Terry et al.
2013/0306084 A1 11/2013 Flick
2014/0000638 A1 * 1/2014 Sebastian ................ A24F 40/30 131/328
2014/0060554 A1 * 3/2014 Collett .................... A24F 40/42 392/386
2014/0060555 A1 3/2014 Chang et al.
2014/0096781 A1 4/2014 Sears et al.
2014/0096782 A1 4/2014 Ampolini et al.
2014/0209105 A1 7/2014 Sears et al.
2014/0253144 A1 9/2014 Novak et al.
2014/0261408 A1 9/2014 DePiano et al.
2014/0261486 A1 9/2014 Potter et al.
2014/0261487 A1 9/2014 Chapman et al.
2014/0261495 A1 9/2014 Novak et al.
2014/0270726 A1 9/2014 Egoyants et al.
2014/0270727 A1 9/2014 Ampolini et al.
2014/0270729 A1 9/2014 DePiano et al.
2014/0270730 A1 9/2014 DePiano et al.
2017/0042231 A1 * 2/2017 Cameron ................ A24F 40/65
2019/0200677 A1 * 7/2019 Chong ..................... A24D 3/17
2022/0322742 A1 * 10/2022 Batley ..................... A24F 40/20
2024/0148063 A1 * 5/2024 Hejazi ..................... A24F 40/46

FOREIGN PATENT DOCUMENTS

| | | |
|---|---|---|
| CL | 2013003637 | 7/2014 |
| CN | 1541577 | 11/2004 |
| CN | 2719043 | 8/2005 |
| CN | 201379072 | 1/2010 |
| CN | 203446534 | 2/2014 |
| CN | 103989252 | 8/2014 |
| EP | 0 295 122 | 12/1988 |
| EP | 0 430 566 | 6/1991 |
| EP | 0 503 767 | 9/1992 |
| EP | 0 845 220 | 6/1998 |
| EP | 1 618 803 | 1/2006 |
| GB | 2469850 | 11/2010 |
| RU | 2 656 195 | 5/2018 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2017/108991 | 6/2017 |
| WO | WO 2017/207419 | 12/2017 |
| WO | WO 2017/211600 | 12/2017 |

* cited by examiner

AEROSOL DELIVERY DEVICE WITH SEGMENTED ELECTRICAL HEATER

CROSS-REFERENCE TO RELATED APPLICATIONS

This application is a continuation of U.S. patent application Ser. No. 17/165,188, filed Feb. 2, 2021, titled Aerosol Delivery Device with Segmented Electrical Heater, which is a continuation of U.S. patent application Ser. No. 16/110,223, filed Aug. 23, 2018, titled Aerosol Delivery Device with Segmented Electrical Heater, each of which is incorporated herein in its entirety by reference.

FIELD OF THE DISCLOSURE

The present disclosure relates to aerosol delivery articles and uses thereof for yielding tobacco components or other materials in an inhalable form. The articles may be made or derived from tobacco or otherwise incorporate tobacco for human consumption. More particularly, the disclosure provides aerosol delivery devices wherein tobacco, a tobacco derived material, or other material is heated, preferably without significant combustion, to provide an inhalable substance, the substance, in the various implementations, being in a vapor or aerosol form. The present disclosure also relates to aerosol delivery devices that include a reservoir and a vaporizing assembly, which may utilize electrical power to heat an aerosol precursor composition for the production of an aerosol.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties. See also, for example, the various types of smoking articles, aerosol delivery devices, and electrically powered heat generating sources referenced by brand name and commercial source in U.S. Pat. App. Pub. No. 2015/0220232 to Bless et al., which is incorporated herein by reference in its entirety. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference in their entireties.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SFO by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™;

Articles that produce the taste and sensation of smoking by electrically heating tobacco, tobacco derived materials, and/or liquids have suffered from inconsistent performance characteristics. Accordingly, it is desirable to provide a smoking article that can provide the sensations of cigarette, cigar, or pipe smoking, and that does so with advantageous performance characteristics.

BRIEF SUMMARY

In various implementations, the present disclosure provides an aerosol delivery device. In one implementation, the aerosol delivery device comprises a control body having an outer housing, an electrical energy source located within the housing, a control component operatively connected to the electrical energy source, a heating assembly operatively connected to the control component, and an aerosol source member that includes an aerosol generating component configured to be positioned proximate the heating assembly. The heating assembly comprises a series of heating members, and each heating member is independent and distinct and configured to heat a segment of the aerosol source member. In some implementations, the heating assembly may comprise a moveable jaw and a stationary jaw, wherein the heating members are located on the moveable jaw, and wherein the moveable jaw may be configured to move between an open position, in which the moveable jaw is spaced from the stationary jaw and the heating members are not in contact with the aerosol source member, and a closed position, in which the series of heating members of the moveable jaw are in contact with the aerosol source member. Some implementations may further comprise a receiving sleeve configured to receive the aerosol source member, and the receiving sleeve may be located, in the closed position, between the moveable jaw and the stationary jaw. In some implementations, the series of heating members may comprise a series of heating pins that are configured, in the closed position, to pass through the aerosol source member and to create an electrical connection with a series of corresponding connectors located on the stationary jaw. In some implementations, the heating pins may have a substantially cylindrical shape. In some implementations, the series of heating members may comprise individual heating elements that are configured, in the closed position, to extend into the aerosol source member. In some implementations, the heating elements may have a substantially blade-like shape. In some implementations, the moveable jaw may be configured to be automatically moveable. In some implementations, the moveable jaw may be configured to be manually moveable.

In some implementations, the series of heating members may comprise a series of individual heating elements, wherein the heating assembly may comprise two or more moveable jaws, wherein one or more of the heating members are located on each moveable jaw, and wherein the moveable jaws may be configured to move between an open position, in which the moveable jaws are spaced from each other and the heating members are not in contact with the aerosol source member, and a closed position, in which the series of heating elements of the respective moveable jaws are in contact with the aerosol source member. In some implementations, the heating assembly may comprise three moveable jaws, and the heating elements of each moveable jaw may have a staggered configuration with respect to another moveable jaw. In some implementations, the heating elements may be configured, in the closed position, to extend into the aerosol source member. In some implementations, the moveable jaws may be configured to be automatically moveable. In some implementations, the moveable jaws may be configured to be manually moveable. In some implementations, the heating assembly may comprises a series of fixed heating elements that are located adjacent the aerosol source member. In some implementations, the aerosol source member may comprise a removable cartridge and the aerosol generating component may comprise a tobacco or tobacco-derived material. In some implementations, the aerosol source member may comprise a removable cartridge and the aerosol generating component may comprise a liquid aerosol precursor composition. In some implementations, the cartridge may define a series of atomizer chambers, and a separate wick may extend through each atomizer chamber. In some implementations, each of the fixed heating elements may be configured to be located proximate a corresponding atomizer chamber. In some implementations, the heating members may be configured to be independently controllable.

These and other features, aspects, and advantages of the disclosure will be apparent from a reading of the following detailed description together with the accompanying drawings, which are briefly described below.

BRIEF DESCRIPTION OF THE DRAWINGS

In order to assist the understanding of implementations of the disclosure, reference will now be made to the appended drawings, in which like reference numerals refer to like elements and which are not necessarily drawn to scale. The drawings are by way of example only and should not be construed as limiting the disclosure.

DETAILED DESCRIPTION

Figure 1:
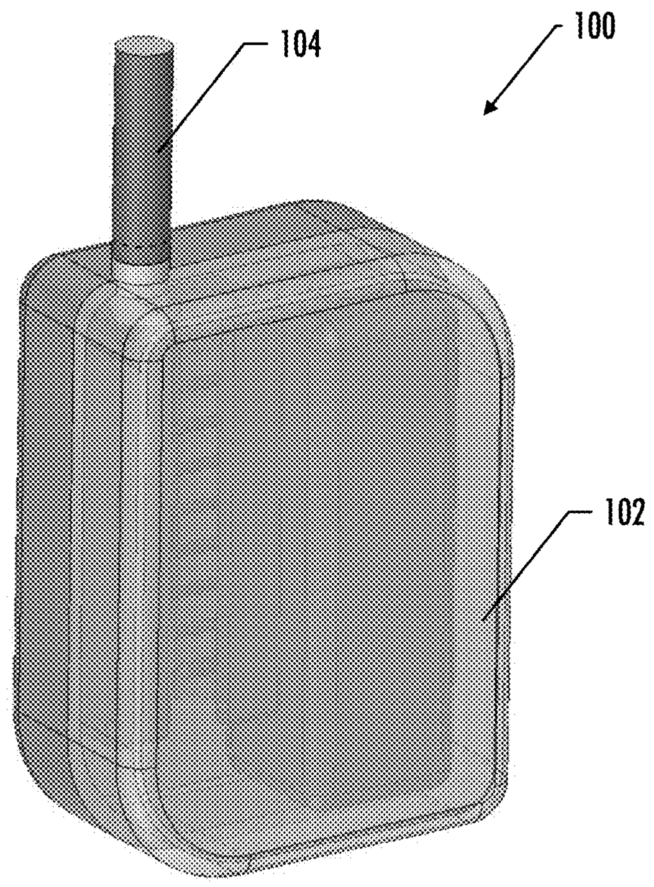
FIG. 1 illustrates a perspective schematic view of an aerosol delivery device, in accordance with an example implementation of the present disclosure.

The present disclosure now will be described more fully hereinafter. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. It must be noted that, as used in this specification, the singular forms "a," "an," and "the" include plural referents unless the context clearly dictates otherwise.

The present disclosure provides articles that use electrical energy to heat a material (preferably without combusting the material to any significant degree) to form an inhalable substance, the articles being sufficiently compact to be considered "hand-held" devices. In certain implementations, the articles can particularly be characterized as smoking articles. As used herein, the term is intended to mean an article that provides the taste and/or the sensation (e.g., hand-feel or mouth-feel) of smoking a cigarette, cigar, or pipe without the actual combustion of any component of the article. The term smoking article does not necessarily indicate that, in operation, the article produces smoke in the sense of the by-product of combustion or pyrolysis. Rather, smoking relates to the physical action of an individual in using the article—e.g., holding the article in a hand, drawing on one end of the article, and inhaling from the article. In further implementations, the inventive articles can be characterized as being vapor-producing articles, aerosolization articles, or pharmaceutical delivery articles. Thus, the articles can be arranged so as to provide one or more substances in an inhalable state. In some implementations, the inhalable substance can be substantially in the form of a vapor (i.e., a substance that is in the gas phase at a temperature lower than its critical point). In other implementations, the inhalable substance can be in the form of an aerosol (i.e., a suspension of fine solid particles or liquid droplets in a gas). The physical form of the inhalable substance is not necessarily limited by the nature of the inventive articles but rather may depend upon the nature of the medium and the inhalable substance itself as to whether it exists in a vapor state or an aerosol state. In some implementations, the terms "vapor" and "aerosol" may be interchangeable. Thus, for simplicity, the terms "vapor" and "aerosol" as used to describe the disclosure are understood to be interchangeable unless stated otherwise.

While the systems are generally described herein in terms of implementations associated with aerosol delivery devices such as so-called "e-cigarettes," or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. In some examples, an elongated body resembling the shape of a cigarette or cigar can be formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. Various other shapes and configurations may be employed in other implementations (e.g., rectangular or fob-shaped).

In one implementation, all of the components of the aerosol delivery device are contained within one outer body or shell. Alternatively, an aerosol delivery device can comprise two or more shells that are joined and are separable. For example, an aerosol delivery device can possess a control body comprising a shell containing one or more reusable components (e.g., a rechargeable battery and various electronics for controlling the operation of that article), and removably attached thereto a disposable portion (e.g., a disposable cartridge or aerosol source member containing aerosol precursor material, flavorant, etc.).

In general, aerosol delivery devices of the present disclosure may generally comprise some combination of an electrical energy source (i.e., an electrical power source), at least one control component (e.g., means for actuating, controlling, regulating and ceasing power for heat generation, such as by controlling electrical current flow from the electrical energy source to other components of the device—e.g., a microprocessor, individually or as part of a microcontroller), a heating member or heat generation component (e.g., a conductive electrical resistance heating member or an inductive heating member), and an aerosol source member that includes an aerosol generating component that is positionable in proximity to or in direct contact with the heating member. When the heating member heats the aerosol generating component, an inhalable substance is formed from, released from, or generated from the aerosol generating component in a physical form suitable for inhalation by a consumer. It should be noted that the foregoing terms are meant to be interchangeable such that reference to release, releasing, releases, or released includes form or generate, forming or generating, forms or generates, and formed or generated. Specifically, the inhalable substance is released in the form of a vapor or aerosol or mixture thereof. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate an electrical energy source (e.g., a battery and/or other electrical power source, such as a capacitor) to provide current flow sufficient to provide various functionalities to the aerosol delivery device, such as powering of a heating member, powering of control systems, powering of indicators, and the like. The power source can take on various implementations. Preferably, the power source is able to deliver sufficient power to rapidly heat the heating member to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the single shell type of unit or within a multi-piece separable shell type of unit of the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

Although a device according to the present disclosure may take on a variety of implementations, as discussed in detail below, the use of the device by a consumer will be similar in scope. In particular, the device may be provided as a plurality of components that are combined by the consumer for use and then are dismantled by the consumer thereafter. Specifically, a consumer may have a reusable control body that is substantially cylindrical, substantially rectangular, substantially cuboidal, or another shape having an opening located in a portion of the control body housing. In some implementations, the housing may also include one or more indicators of active use of the device (e.g., one or more indicator lights, indicia displayed on an electronic display, haptic feedback, some combination thereof, etc.). In some implementations, one or more aerosol source members may engage or may be received in the opening of the control body. To use the article, the consumer may insert the aerosol source member into the opening or otherwise combine the aerosol source member with the control body so that the device is operable as discussed herein. In some implementations, the aerosol source member may be inserted as far into the control body as allowed by the overall structure of the components and/or other internal receiving features. In some examples, at least a portion of the aerosol source member that is at least sufficiently sized for insertion into the mouth of the consumer for puffing thereon will remain outside of the control body. This may be referred to as the mouth end of the aerosol source member. In other examples a portion of the aerosol delivery device itself may be at least sufficiently sized for insertion into the mouth of the consumer. This may be referred to as the mouth end of the aerosol delivery device.

During use, the consumer initiates heating of a heating member that is adjacent an aerosol generating component (or a specific portion thereof) of the aerosol source member, and heating of the component releases the inhalable substance within a space inside the housing and/or the aerosol source member so as to yield an inhalable substance. When the consumer inhales on the mouth end of the aerosol source member or the mouth end of the aerosol delivery device, air is drawn into and/or past the aerosol source member (such as, for example, through openings in the aerosol delivery device and/or the aerosol source member itself). The combination of the drawn air and the released inhalable substance is inhaled by the consumer as the drawn materials exit the mouth end of the aerosol source member or the mouth end of the aerosol delivery device into the mouth of the consumer. In some implementations, to initiate heating, the consumer may manually actuate a pushbutton or similar component that causes the heating member to receive electrical energy from the battery or other power source. The electrical energy may be supplied for a pre-determined length of time or may be manually controlled. Preferably, flow of electrical energy does not substantially proceed in between puffs on the device (although energy flow may proceed to maintain a baseline temperature greater than ambient temperature—e.g., a temperature that facilitates rapid heating to the active heating temperature). In other implementations, heating may be initiated by the puffing action of the consumer through use of various sensors, as otherwise described herein. Once the puff is discontinued, heating may stop or be reduced. When the consumer has taken a sufficient number of puffs so as to have released a sufficient amount of the inhalable substance (e.g., an amount sufficient to equate to a typical smoking experience), the aerosol source member may be removed from the control body and discarded.

Figure 2:
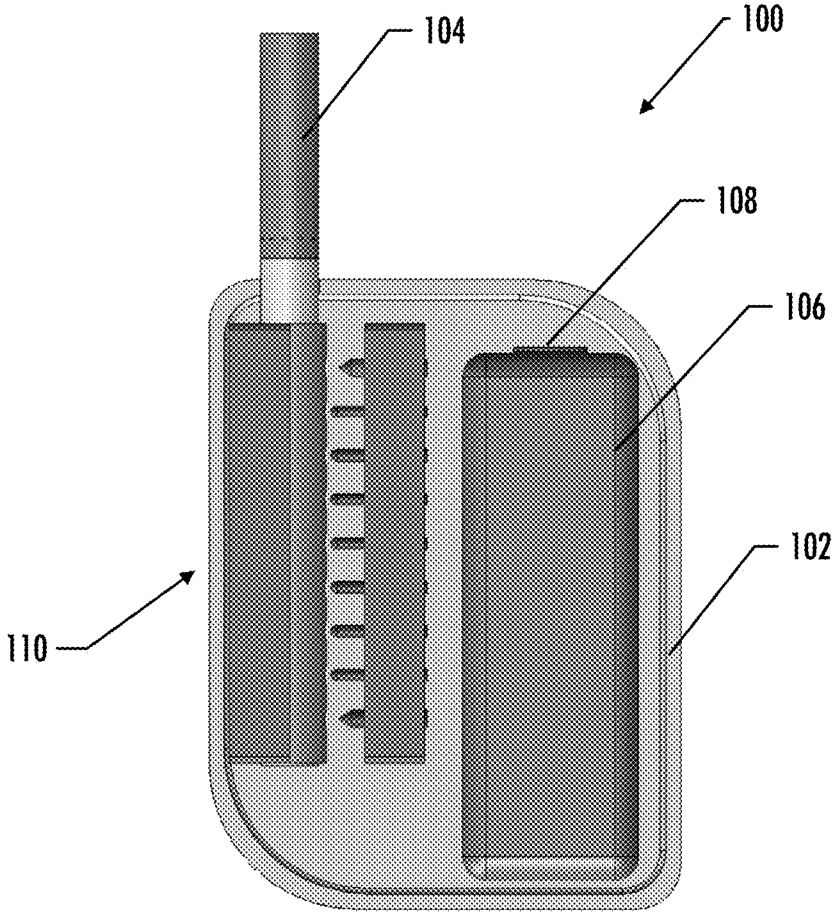
FIG. 2 illustrates a front schematic view of an aerosol delivery device, in accordance with an example implementation of the present disclosure.

FIG. 1 illustrates a perspective view of an aerosol delivery device 100, in accordance with example implementations of the present disclosure. In particular, FIG. 1 depicts an aerosol delivery device 100 that includes a housing 102 and an aerosol source member 104. FIG. 2 illustrates a front view of the aerosol delivery device 100, wherein a portion of the housing 102 has been removed to reveal some internal components thereof. In particular, the aerosol delivery device 100 of the depicted implementation further includes an electrical energy source 106 (e.g., a battery, which may be rechargeable, and/or a rechargeable supercapacitor), a control component, 108 (e.g., a microprocessor, individually or as part of a microcontroller, a printed circuit board (PCB) that includes a microprocessor and/or microcontroller, etc.), and a heating assembly 110. As will be discussed in more detail below, the heating assembly 110 of various implementations comprises a series of independent and distinct heating members, wherein each heating member is configured to heat a segment of the aerosol source member 104.

In various implementations, one or both of the control component 108 and the electrical energy source 106 may be coupled with the housing 102. For the sake of the current application, the phrase "coupled with" when used with respect to one component relative to another may encompass implementations in which one component is located within another component and/or implementations wherein one component is separate but otherwise operatively connected to another component. For example, in the depicted implementation, both the control component 108 and the electrical energy source 106 are located within the housing 102; however, in other implementations one or both of the control component 108 and the electrical energy source 106 may be separate components. Further information regarding the control component 108 and the electrical energy source 106 is provided below.

In some implementations, the housing 102 may also include one or more pushbuttons configured to activate certain operations of the device 100, such as, for example, turning on the device and initiating heating of the heating assembly 110 (e.g., one or more heating members of the heating assembly). As will be discussed in more detail below, in various implementations, the aerosol source member 104 may comprise a heated end, which is configured to be inserted into the housing 102, and a mouth end, upon which a user draws to create the aerosol. It should be noted that while the aerosol delivery device 100 of FIG. 1 is shown as having a substantially rectangular or fob-shaped housing 102 for ease of illustration, in other implementations the housing 102 may have any other shape including an elongated shell or body that may be substantially tubular in shape and, as such, resemble the shape of a conventional cigarette or cigar, and thus the components described below may be sized and configured to fit inside an elongated body.

In specific implementations, one or both of the housing 102 and the aerosol source member 104 may be referred to as being disposable or as being reusable. For example, the electrical energy source 106 may comprise a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 104 may comprise a single-use device. A single use component for use with a control body is disclosed in U.S. Pat. No. 8,910,639 to Chang et al., which is incorporated herein by reference in its entirety.

In various implementations, the control component 108 may comprise a control circuit (which may be connected to further components, as further described herein) that may be connected by electrically conductive wires to the electrical energy source 106. In various implementations, the control component 108 may control when and how the heating assembly 110 (e.g., one or more heating members of the heating assembly) receives electrical energy to heat the aerosol generating component of the aerosol source member 104 for release of the inhalable substance for inhalation by a consumer. Such control can relate to actuation of pressure sensitive switches or the like, which are described in greater detail hereinafter. It should be noted that the terms "connected" or "coupled" should not be read as necessitating direct connection without an intervening component. Rather, these terms may encompass direct connection and/or connection via one or more intervening components. As such, in various implementations these terms may be understood to mean operatively connected to or operatively coupled with. In various implementations, the control component of the present disclosure may comprise the control components and methods described in U.S. patent application Ser. No. 15/976,526, filed on May 10, 2018, and titled Control Component for Segmented Heating in an Aerosol Delivery Device, which is incorporated herein by reference in its entirety.

In some implementations, the control component 108 may be configured to closely control the amount of heat provided to the aerosol generating component. While the heat needed to volatilize the aerosol-forming substance in a sufficient volume to provide a desired dosing of the inhalable substance for a single puff can vary for each particular substance used, it can be particularly useful for the heating assembly to heat to a temperature of at least 120° C., at least 130° C., or at least 140° C. In some implementations, in order to volatilize an appropriate amount of the aerosol-forming substance and thus provide a desired dosing of the inhalable substance, the heating temperature may be at least 150° C., at least 200° C., at least 300° C., or at least 350° C. It can be particularly desirable, however, to avoid heating to temperatures substantially in excess of about 550° C. in order to avoid degradation and/or excessive, premature volatilization of the aerosol-forming substance. It should be noted that in some implementations, the heating process may include different stages. For example, some implementations may include a preheating stage in which the heating assembly (e.g., each of the individual heating elements) may heat to approximately 100° C. Then, depending on activation of any individual heater (e.g., such as being activated by push button, etc.) the temperature of that specific heater may increase as noted above. Heating specifically should be at a sufficiently low temperature and sufficiently short time so as to avoid significant combustion (preferably any combustion) of the aerosol generating component. The present disclosure may particularly provide the components of the present article in combinations and modes of use that will yield the inhalable substance in desired amounts at relatively low temperatures. As such, yielding can refer to one or both of generation of the aerosol within the article and delivery out of the article to a consumer. In specific implementations, the heating temperature may be about 120° C. to about 300° C., about 130° C. to about 290° C., about 140° C. to about 280° C., about 150° C. to about 250° C., or about 160° C. to about 200° C. The duration of heating can be controlled by a number of factors, as discussed in greater detail hereinbelow. Heating temperature and duration may depend upon the desired volume of aerosol and ambient air that is desired to be drawn through the aerosol source member, as further described herein. The duration, however, may be varied depending upon the heating rate of the heating assembly, as the article may be configured such that the heating members are energized only until a desired temperature is reached. Alternatively, duration of heating may be coupled to the duration of a puff on the article by a consumer. Generally, the temperature and time of heating will be controlled by one or more components contained in the control body, as noted above.

The amount of inhalable material released by the aerosol source member can vary based upon the nature of the aerosol generating component. Preferably, the aerosol source member is configured with a sufficient amount of the aerosol generating component, with a sufficient amount of any aerosol-former, and to function at a sufficient temperature for a sufficient time to release a desired amount over a course of use. The amount may be provided in a single inhalation from the aerosol source member or may be divided so as to be provided through a number of puffs from the article over a relatively short length of time (e.g., less than 30 minutes, less than 20 minutes, less than 15 minutes, less than 10 minutes, or less than 5 minutes). For example, the device may provide nicotine in an amount of about 0.01 mg to about 0.1 mg, about 0.05 mg to about 1.0 mg, about 0.08 mg to about 0.5 mg, about 0.1 mg to about 0.3 mg, or about 0.15 mg to about 0.25 mg per puff on the aerosol source member. In other implementations, a desired amount may be characterized in relation to the amount of wet total particulate matter delivered based on puff duration and volume. For example, the aerosol source member may deliver at least 1.0 mg of wet total particulate matter on each puff, for a defined number of puffs (as otherwise described herein), when smoked under standard FTC smoking conditions of 2 second, 35 ml puffs. Such testing may be carried out using any standard smoking machine. In other implementations, the amount of total particulate matter (TPM) yielded under the same conditions on each puff may be at least 1.5 mg, at least 1.7 mg, at least 2.0 mg, at least 2.5 mg, at least 3.0 mg, about 1.0 mg to about 5.0 mg, about 1.5 mg to about 4.0 mg, about 2.0 mg to about 4.0 mg, or about 2.0 mg to about 3.0 mg, at least 3 mg to about 7 mg, about 4 mg to about 8 mg, and about 5 mg to about 10 mg.

As noted, the aerosol delivery device 100 of some implementations may include a pushbutton, which may be linked to the control component for manual control of the heating members. For example, in some implementations the consumer may use the pushbutton to energize the heating assembly 110. Similar functionality tied to the pushbutton may be achieved by other mechanical means or non-mechanical means (e.g., magnetic or electromagnetic). Thusly, activation of the heating assembly 110 may be controlled by a single pushbutton. Alternatively, multiple pushbuttons may be provided to control various actions separately. In some implementations, one or more pushbuttons present may be substantially flush with the casing of the housing 102.

Instead of (or in addition to) any pushbuttons, the aerosol delivery device 100 of the present disclosure may include components that energize the heating assembly 110 in response to the consumer's drawing on the article (i.e., puff-actuated heating). For example, the device may include a switch or flow sensor (not shown) in the housing 102 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch, or a touch sensor (e.g., capacitive touch sensor) configured to sense contact between a user (e.g., mouth or fingers of user) and one or more surfaces of the aerosol delivery device 100. An example mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the consumer draws on the device. In addition, flow sensing devices, such as those using hot-wire anemometry principles, may be used to cause the energizing of the heating assembly sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and aerosol source member 104 may be included in the housing 102 so that pressure changes during draw are readily identified by the switch. Other example puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In some implementations, when the consumer draws on the mouth end of the aerosol source member 104, the current actuation means may permit unrestricted or uninterrupted flow of current through the heating assembly to generate heat rapidly. Because of the rapid heating, it can be useful to include current regulating components to (i) regulate current flow through the heating assembly to control heating of the heating assembly and the temperature experienced thereby, and (ii) prevent overheating and degradation of the aerosol generating component. In some implementations, the current regulating circuit may be time-based. Specifically, such a circuit may include a means for permitting uninterrupted current flow through the heating member for an initial time period during draw, and a timer means for subsequently regulating current flow until draw is completed. For example, the subsequent regulation can include the rapid on-off switching of current flow (e.g., on the order of about every 1 to 50 milliseconds) to maintain the heating assembly (or one or more heating members of the heating assembly) within the desired temperature range. Further, regulation may comprise simply allowing uninterrupted current flow until the desired temperature is achieved then turning off the current flow completely. The heating assembly (or one or more heating members of the heating assembly) may be reactivated by the consumer initiating another puff on the article (or manually actuating the pushbutton, depending upon the specific switch implementation employed for activating the heater). Alternatively, the subsequent regulation can involve the modulation of current flow through the heating assembly (or one or more heating members of the heating assembly) to maintain the heating assembly (or one or more heating members of the heating assembly) within a desired temperature range. In some implementations, so as to release the desired dosing of the inhalable substance, the heating assembly (or one or heating members of the heating assembly) may be energized for a duration of about 0.2 second to about 5.0 seconds, about 0.3 second to about 4.0 seconds, about 0.4 second to about 3.0 seconds, about 0.5 second to about 2.0 seconds, or about 0.6 second to about 1.5 seconds. One example time-based current regulating circuit can include a transistor, a timer, a comparator, and a capacitor. Suitable transistors, timers, comparators, and capacitors are commercially available and will be apparent to the skilled artisan. Example timers are those available from NEC Electronics as C-1555C and from General Electric Intersil, Inc. as ICM7555, as well as various other sizes and configurations of so-called “555 Timers”. An example comparator is available from National Semiconductor as LM311. Further description of such time-based current regulating circuits is provided in U.S. Pat. No. 4,947,874 to Brooks et al., which is incorporated herein by reference in its entirety.

In light of the foregoing, it can be seen that a variety of mechanisms can be employed to facilitate actuation/deactuation of current to the heating assembly (or one or more members of the heating assembly). For example, the device may include a timer for regulating current flow in the article (such as during draw by a consumer). The device may further include a timer responsive switch that enables and disables current flow to the heating member. Current flow regulation also can comprise use of a capacitor and components for charging and discharging the capacitor at a defined rate (e.g., a rate that approximates a rate at which the heating member heats and cools). Current flow specifically may be regulated such that there is uninterrupted current flow through the heating member for an initial time period during draw, but the current flow may be turned off or cycled alternately off and on after the initial time period until draw is completed. Such cycling may be controlled by a timer, as discussed above, which can generate a preset switching cycle. In specific implementations, the timer may generate a periodic digital wave form. The flow during the initial time period further may be regulated by use of a comparator that compares a first voltage at a first input to a threshold voltage at a threshold input and generates an output signal when the first voltage is equal to the threshold voltage, which enables the timer. Such implementations further can include components for generating the threshold voltage at the threshold input and components for generating the threshold voltage at the first input upon passage of the initial time period.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties. Another method uses an electrical resistance change for actuating the aerosol delivery device and/or the heating assembly thereof. It works by using a very thin small metallic probe in the form of strip or wire that is installed perpendicular to the air flow inside the cartridge. The air flow generated by the user applies mechanical force on the probe and folds it to some extent. Due to this change in geometry that results in bending/tension in part of the probe, a change in electrical resistance of the probe occurs, this resistance alteration is sent as a pulse/information to the PCB and works as a trigger to activate the heating assembly 110.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. patent application Ser. No. 14/881,392 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

As noted above, the electrical energy source 106 used to provide power to the various electrical components of the device 100 may take on various implementations. Preferably, the electrical energy source is able to deliver sufficient energy to rapidly heat the heating assembly in the manner described above and power the device through use with multiple aerosol source members 104 while still fitting conveniently in the device 100. Examples of useful electrical energy sources include lithium-ion batteries that are preferably rechargeable (e.g., a rechargeable lithium-manganese dioxide battery). In particular, lithium polymer batteries can be used as such batteries can provide increased safety. Other types of batteries—e.g., nickel-cadmium cells, lithium-metal cells, lithium-Sulphur batteries, lithium-air batteries, nanowire batteries, graphene batteries, foam batteries—may also be used. Additionally, a preferred electrical energy source is of a sufficiently light weight to not detract from a desirable smoking experience. Some examples of possible electrical energy sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

One example of an electrical energy source is a TKI-1550 rechargeable lithium-ion battery produced by Tadiran Batteries GmbH of Germany. In another implementation, a useful electrical energy source may be a N50-AAA CADNICA nickel-cadmium cell produced by Sanyo Electric Company, Ltd., of Japan. In other implementations, a plurality of such batteries, for example providing 1.2-volts each, may be connected in series. Other electrical energy sources, such as rechargeable lithium-manganese dioxide batteries, may also be used. Any of these batteries or combinations thereof may be used in the electrical energy source, but rechargeable batteries are preferred because of cost and disposal considerations associated with disposable batteries. In implementations where rechargeable batteries are used, the aerosol delivery device 100 may further include charging contacts for interaction with corresponding contacts in a conventional recharging unit (not shown) deriving power from a standard 120-volt AC wall outlet, or other sources such as an automobile electrical system or a separate portable power supply. In further implementations, the electrical energy source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the device 100. Thus, the present disclosure also may include a charger component that can be attached to the device between uses to replenish the supercapacitor. Thin film batteries may be used in certain implementations of the present disclosure.

As noted above, in various implementations, the aerosol delivery device 100 may comprise one or more indicators (not shown). In various implementations, one or more indicators may be located at any location on the housing 102. In some implementations, the indicators may be lights (e.g., light emitting diodes) that may provide indication of multiple aspects of use of the device. For example, a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In other implementations, a series of lights might correspond to the series of heating members, such that if one or more of the heating members is activated, the corresponding light may be lit. In still other implementations, only a single indicator may be present, and lighting thereof may indicate that current is flowing to the heating assembly and the device is actively heating. This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In various implementations, the housing 102 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as further discussed herein. In some implementations, a heat resistant polymer may be used. In other implementations, ceramic materials may be used. In further implementations, an insulating material may be used so as not to unnecessarily move heat away from the aerosol source member. The housing, when formed of a single layer, may have a thickness that preferably is about 0.2 mm to about 5.0 mm, about 0.5 mm to about 4.0 mm, about 0.5 mm to about 3.0 mm, or about 1.0 mm to about 3.0 mm. Further example types of components and materials that may be used to provide the functions described above or be used as alternatives to the materials and components noted above can be those of the types set forth in U.S. Pat. App. Pub. Nos. 2010/00186757 to Crooks et al.; 2010/00186757 to Crooks et al.; and 2011/0041861 to Sebastian et al.; the disclosures of the documents being incorporated herein by reference in their entireties.

Figure 3:
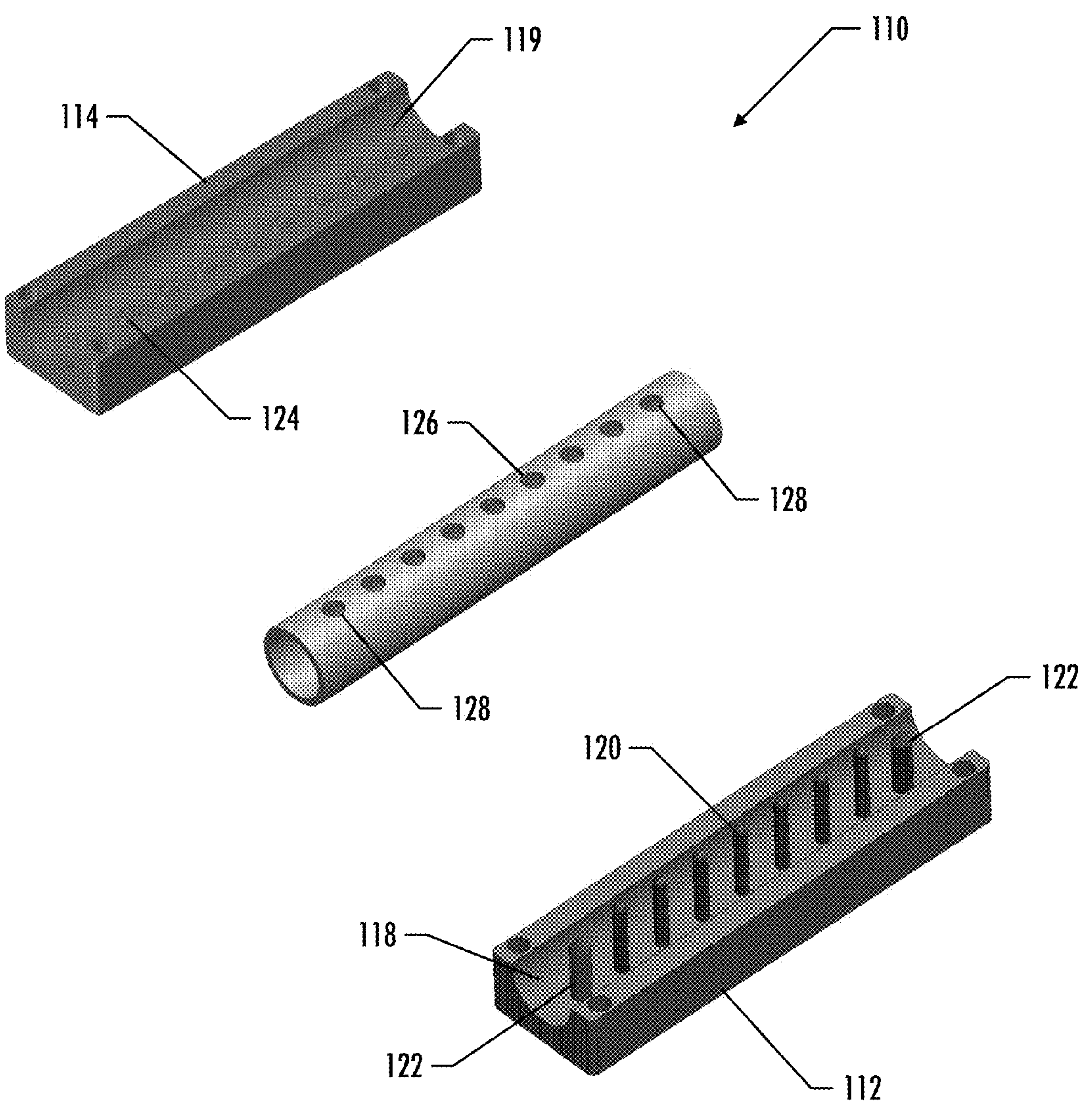
FIG. 3 illustrates a perspective view of certain components of a heating assembly of an aerosol delivery device, in accordance with an example implementation of the present disclosure.
Figure 4:
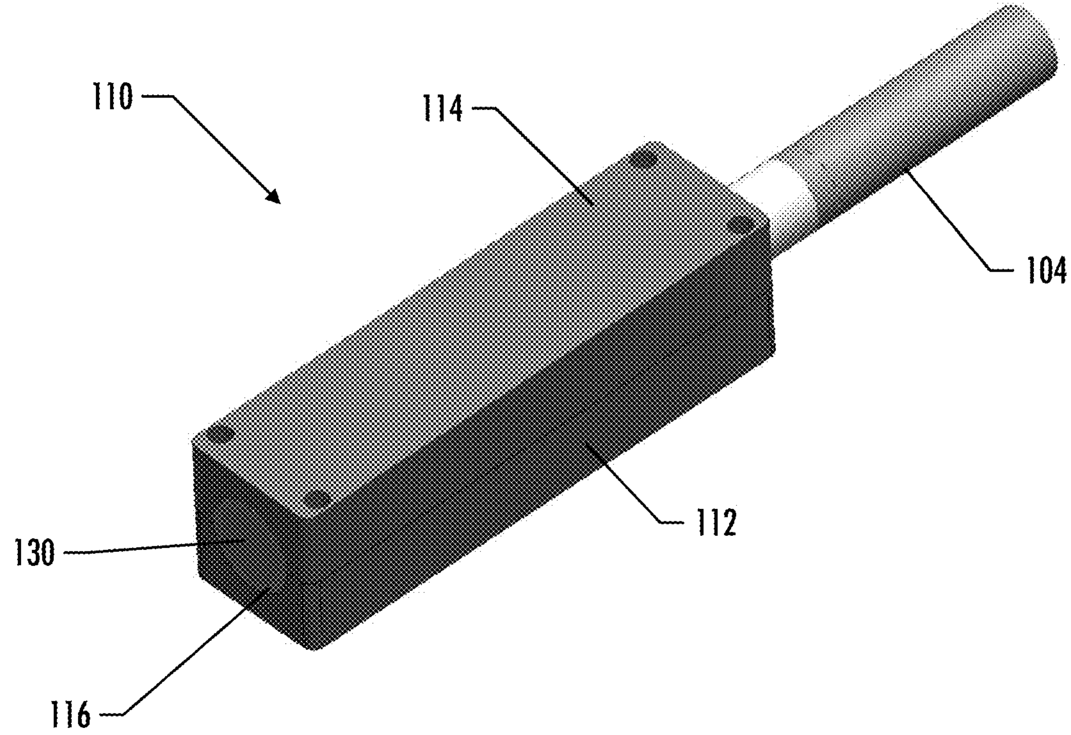
FIG. 4 illustrates a perspective view of certain components of a heating assembly and an aerosol source member of an aerosol delivery device, in accordance with an example implementation of the present disclosure.

FIG. 3 illustrates a perspective view of certain components of the heating assembly 110 of the aerosol delivery device 100 of FIGS. 1 and 2, in accordance with an example implementation of the present disclosure, and FIG. 4 illustrates a perspective view of certain components of the heating assembly 110 with an aerosol source member 104 located in the receiving sleeve 116, in accordance with an example implementation of the present disclosure. In particular, the heating assembly 110 of the depicted implementation includes a moveable jaw 112, a stationary jaw 114 (rotated upside down in the drawing, for clarity of illustration), and a receiving sleeve 116. Although other materials are possible, in the depicted implementation, the moveable jaw 112, the stationary jaw 114, and/or the receiving sleeve 116 may be made of metal materials (e.g., aluminum, stainless steel, metal alloys, etc.), ceramic materials (e.g., alumina, silica, mullite, silicon carbide, silicon nitride, aluminum nitride, etc.), polymers (e.g., polyimide, thermoplastic polyimide, polybenzimidazole, polyether ether ketone, polypropylene, high density polyethylene, etc.) composite materials, and/or any combinations thereof. As will be discussed in more detail below, the moveable jaw 112 of the depicted implementation is configured to move between an open position, in which the moveable jaw is spaced from the stationary jaw 114 and the receiving sleeve 116, and a closed position, in which the moveable jaw 112 is adjacent the stationary jaw 114, and the receiving sleeve 116 is in between the moveable jaw 112 and the stationary jaw 114. In the depicted implementation, the receiving sleeve 116 has a substantially cylindrical shape configured to receive at least the heated end of the aerosol source member 104; however, in other implementations the receiving sleeve may have any other shape, such as any shape that is complementary of the shape of the heated end of the aerosol source member. In the depicted implementation, each of the moveable jaw 112 and the stationary jaw 114 has an internal shape configured to substantially surround the receiving sleeve 116 and thus at least the heated end of the aerosol source member 104. In particular, an interior surface 118 of the moveable jaw 112 and an interior surface 119 of the stationary jaw 114 together form a shape complementary of the shape of the receiving sleeve 116. In such a manner, when the moveable jaw 112 is in the closed position, the internal surfaces 118, 119 come together to surround the receiving sleeve 116.

The moveable jaw 112 of the depicted implementation includes a series of heating pins 120, which extend outward from the internal surface 118 thereof. The moveable jaw 112 of the depicted implementation also includes a pair of locating pins 122, which extend outward from the internal surface 118 of the moveable jaw 112. It should be noted that in some implementations there need not be any locating pins 122 as the heating pins may also serve this function. In various implementations, the series of heating pins 120 are configured to electrically connect (in the closed position) with a series of corresponding connectors 124, which are located on the internal surface 119 of the stationary jaw 114. In addition, the receiving sleeve 116 includes two opposing rows of openings 126, which, in operation, align with the series of heating pins 120 and the series of connectors 124. In addition, a pair of end openings 128 is configured to align with the locating pins 122. When the moveable jaw 112 is in in the closed position, the series of heating pins 120 extend through corresponding openings 126 of the receiving sleeve 116 and into electrical contact with the corresponding connectors 124 of the stationary jaw 120. The locating pins 122 of the depicted implementation also extend through a pair of corresponding openings 128 of the receiving sleeve but do not make electrical contact with the stationary jaw 114; however, in some implementations the locating pins 122 may also make electrical contact. In the depicted implementation, there are seven heating pins 120 and thus there are seven corresponding connectors 124 and seven corresponding openings 126; however, in other implementations any number of heating pins 120, connectors 124, and openings 126 may be used. In the depicted implementation the heating pins have a substantially cylindrical shape with a rounded end; however, in other implementations, the heating pins 120 may have other shapes, and in still other implementations, the heating pins 120 need not have the same shape.

The heating pins 120 of the depicted implementation comprise resistive heating members when the electrical connection is made with the corresponding connectors 124. Resistive heating members may be configured to produce heat when an electrical current is directed therethrough. Such heating members often comprise a metal material or electrically conductive ceramics and are configured to produce heat as a result of the electrical resistance associated with passing an electrical current therethrough. While in some implementations, the material of the heating pins may be the same throughout, the heating pins 120 of the depicted implementation include electrically conductive materials on each end (e.g., the ends of the heating pins 120 that contact the connectors 124 and the ends of the heating pins 120 connected to the control component 108 and/or electrical energy source 106) and an electrically resistant material in between (e.g., the portion of the heating pins 120 that is configured to contact the aerosol forming component. Examples of the electrically resistant materials may include, but are not limited to, titanium, silver, nickel, nichrome, stainless steel, various metal alloys, ceramics such as silicon carbide and silicon nitride, composites, and/or any combination thereof. Examples of the electrically conductive materials, may include, but are not limited to, copper, aluminum, platinum, gold, silver, iron, steel, brass, bronze, graphite, and/or any combination thereof. A variety of conductive substrates that may be usable with the present disclosure are described in U.S. Pat. App. Pub. No. 2013/0255702 to Griffith et al., the disclosure of which is incorporated herein by reference in its entirety. In some implementations, the heating pins may include resistive traces on the surfaces thereof. In such implementations, for example, the resistive traces may be added to the pins via a variety of techniques including, for example, molding, printing, embedding, machining, squeeze casting, vapor deposition, etc.

As noted, the receiving sleeve 116 of the depicted implementation is configured to receive the heated end of the aerosol source member 104, which may include an aerosol generating component 130. In the open position (shown, for example, in FIG. 2), the moveable jaw 112 is spaced from the stationary jaw 114, as well as the receiving sleeve 116 and aerosol source member 104, and in the closed position (shown for example in FIG. 4), the moveable jaw 112 is adjacent the stationary jaw 114, with the receiving sleeve 116 and aerosol source member 104 disposed in between. In various implementations, actuation between the open position and the closed position (and vice versa) may be accomplished in a variety ways, including, for example, manually, such as by a consumer pressing the jaws together, or automatically or semi-automatically, such as by using a hydraulic gas spring or other force-displacement mechanism that transfers directional force to the moveable jaw 112. Another example may include a linear displacement motor or other actuator configured to displace the moveable jaw 112 between the open and closed positions. Other examples include a piezo actuator, an ultrasonic ceramic actuator, a rotating coil system, a lead screw system, a cam follower mechanism, a gear mechanism, a linkage, and/or any other system configured for generating and transferring directional motion to the moveable jaw 112. Regardless of the mechanism, this motion may be activated via a pushbutton and/or via use of the device (such as, for example, by powering the device, by drawing on the aerosol source member, or by inserting an aerosol source member into the device) as similarly discussed above. In addition to those described above, another method for actuating the moveable jaw 112 operates by means of a small thin metallic probe, such as in the form of strip or wire, that is installed perpendicular to the air flow inside the device 100. The air flow generated by the user applies mechanical force on the probe and folds or bends to some extent. Due to the change in the geometry that results in bending/tension of the probe, a change in electrical resistance of the probe occurs. This resistance alteration is sent as a pulse and/or signal to the control component 108 and works as a trigger to activate the moveable jaw 112.

In the closed position, each heating pin 120 completes an electrical circuit so as to create an independent and distinct heating circuit that is capable of heating, via the heating pin 120, a segment of the aerosol source member. In the open position, however, each circuit is incomplete and the heating pins are incapable of heating. In various implementations, the control component 108 may independently control each of the heating circuits. In such a manner, in the closed position, each of the heating pins 120 may heat a segment of the aerosol source member independently, as controlled by the control component 108. Therefore, in some applications the heating pins 120 may sequentially heat segments of the aerosol source member, while in other applications the heating pins 120 may heat certain groups of segments of the aerosol source member. As will be appreciated, the present disclosure contemplates all of the different heating conditions afforded by using independently controlled heating pins 120. As will be discussed in more detail below, in some implementations heating pin control may occur via the user (such as, for example, via a push button or a control panel) on the device. In addition, various indicators may also indicate which heaters have been used and which heaters have not been used for a consumable used in the device.

It should be noted that while in the depicted implementation there are a total of seven distinct heating pins 120 corresponding to seven distinct heating segments of the aerosol source member 104, in various other implementations the heating assembly 110 may have any number of distinct heating members corresponding to any number of discrete heating segments of the aerosol source member. Further, while in the depicted implementation there a plurality of discrete heating member positions and corresponding discrete heating segments that are spaced apart from each other, in other implementations the discrete positions and corresponding discrete segments may have different spacing, including, but not limited to, spacing that results in the discrete positions and corresponding discrete segments abutting each other and/or overlapping each other, as well as inconsistent spacing.

In the depicted implementation, the heating pins 120 are configured to pierce through the aerosol generating component 130 of the aerosol source member, which is contained in the aerosol source member 104 received in the receiving sleeve 116, and make electrical contact with the connectors 124 of the stationary jaw 114. As such, the aerosol generating component 130 of the depicted implementation comprises a solid or semi-solid material (such as, for example, a tobacco or tobacco-derived material, a medicinal material, an herbal material, etc.). In other implementations, however, the aerosol generating component may comprise a gel, liquid, or semi-liquid material.

As noted, in various implementations the aerosol generating component may comprise a solid or semi-solid material that may be a tobacco or tobacco-derived material. In some implementations, such a material may comprise tobacco-containing beads, tobacco shreds, tobacco strips, reconstituted tobacco material (e.g., an extruded or caste sheet substrate), or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Gels and suspensions may also be utilized. Some representative types of solid and semi-solid aerosol generating component constructions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein.

In various implementations, the aerosol source member, or a portion thereof, may be wrapped in an overwrap material, which may be formed of any material useful for providing additional structure and/or support for the aerosol source member. In various implementations, the overwrap material may comprise a material that resists (or promotes) transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material can incorporate inorganic components. In various implementations, the overwrap may be formed of multiple layers, such as an underlying, bulk layer, and an overlying layer, such as a typical wrapping paper in a cigarette. Such materials may include, for example, lightweight "rag fibers" such as flax, hemp, sisal, rice straw, and/or esparto. Further discussions relating to the configurations for overwrap materials that may be used with the present disclosure may be found in U.S. Pat. No. 9,078,473 to Worm et al., which is incorporated herein by reference in its entirety. In additional implementations, the overwrap material may have or more of the following qualities: it may be impermeable to the transfer of aerosol, it may have the ability to withstand the elevated temperature under consideration, it may promote the transfer of heat in the radial direction from the heater to the tobacco stick material, it may resist the transfer of heat in the axial direction along the tobacco stick away from the segment being heated, and/or it may have relatively low thermal mass so that it does not inhibit rapid temperature rises of the segment being heated. In one implementation, the overwrap material may be a stainless steel foil that, in some implementations, may be approximately 0.001" thick. In another implementation, the overwrap material may be an aluminum foil.

In various implementations, the mouth end of an aerosol source member may include a filter, which may, for example, be made of a cellulose acetate, polypropylene, or polylactic acid material. In various implementations, the filter may increase the structural integrity of the mouth end of the aerosol source member, and/or provide filtering capacity, if desired, and/or provide resistance to draw. For example, an article according to the disclosure can exhibit a pressure drop of about 50 to about 250 mm water pressure drop at 17.5 cc/second air flow. In further implementations, pressure drop can be about 60 mm water to about 180 mm water or about 70 mm water to about 150 mm water. Pressure drop value may be measured using a Filtrona Filter Test Station (CTS Series) available from Filtrona Instruments and Automation Ltd or a Quality Test Module (QTM) available from the Cerulean Division of Molins, PLC. The length of the filter at the mouth end of the aerosol source member can vary—e.g., about 2 mm to about 20 mm, about 5 mm to about 20 mm, or about 10 mm to about 15 mm. In some implementations, the filter may comprise discrete segments. For example, some implementations may include a segment providing filtering, a segment providing draw resistance, a hollow segment providing a space for the aerosol to cool, a segment providing increased structural integrity, other filter segments, and any one or any combination of the above. In some implementations, the filter may be separate from the overwrap, and the filter may be held in position by the overwrap.

Additional example types of overwrapping materials, wrapping material components, and treated wrapping materials that may be used in overwrap in the present disclosure are described in U.S. Pat. No. 5,105,838 to White et al.; U.S. Pat. No. 5,271,419 to Arzonico et al.; U.S. Pat. No. 5,220,930 to Gentry; U.S. Pat. No. 6,908,874 to Woodhead et al.; U.S. Pat. No. 6,929,013 to Ashcraft et al.; U.S. Pat. No. 7,195,019 to Hancock et al.; U.S. Pat. No. 7,276,120 to Holmes; U.S. Pat. No. 7,275,548 to Hancock et al.; PCT WO 01/08514 to Fournier et al.; and PCT WO 03/043450 to Hajaligol et al., which are incorporated herein by reference in their entireties. Representative wrapping materials are commercially available as R. J. Reynolds Tobacco Company Grades 119, 170, 419, 453, 454, 456, 465, 466, 490, 525, 535, 557, 652, 664, 672, 676 and 680 from Schweitzer-Maudit International. The porosity of the wrapping material can vary, and frequently is between about 5 CORESTA units and about 30,000 CORESTA units, often is between about 10 CORESTA units and about 90 CORESTA units, and frequently is between about 8 CORESTA units and about 80 CORESTA units.

To maximize aerosol and flavor delivery which otherwise may be diluted by radial (i.e., outside) air infiltration through the overwrap, one or more layers of non-porous cigarette paper may be used to envelop the aerosol source member (with or without the overwrap present). Examples of suitable non-porous cigarette papers are commercially available from Kimberly-Clark Corp. as KC-63-5, P878-5, P878-16-2 and 780-63-5. Preferably, the overwrap is a material that is substantially impermeable to the vapor formed during use of the inventive article. If desired, the overwrap can comprise a resilient paperboard material, foil-lined paperboard, metal, polymeric materials, or the like, and this material can be circumscribed by a cigarette paper wrap. The overwrap may comprise a tipping paper that circumscribes the component and optionally may be used to attach a filter material to the aerosol source member, as otherwise described herein. In various implementations, other components may exist between the aerosol generating component and the mouth end of the aerosol source member, wherein the mouth end may include a filter. For example, in some implementations one or any combination of the following may be positioned between the aerosol generating component and the mouth end: an air gap; phase change materials for cooling air; flavor releasing media; ion exchange fibers capable of selective chemical adsorption; aerogel particles as filter medium; and other suitable materials.

Tobacco materials useful in the present disclosure can vary and can include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT WO 02/37990 to Bereman; and Bombick et al., *Fund. Appl. Toxicol.,* 39, p. 11-17 (1997); which are incorporated herein by reference in their entireties. Further example tobacco compositions that can be useful in a smoking device, including according to the present disclosure, are disclosed in U.S. Pat. No. 7,726,320 to Robinson et al., which is incorporated herein by reference in its entirety.

Still further, the aerosol generating component may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol generating component may comprise a blend of flavorful and aromatic tobaccos in cut filler form. In another aspect, the aerosol generating component may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entireties.

In some implementations, the aerosol generating component may include tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a burn retardant (e.g., diammonium phosphate and/or another salt) configured to help prevent ignition, pyrolysis, combustion, and/or scorching of the aerosol delivery component by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

In some implementations, other flame/burn retardant materials and additives may be included within the aerosol generating component and my include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the aerosol generating component and/or other components (whether alone or in combination with each other and/or other materials), the desirable properties are preferably provided without undesirable off-gassing, chemically reactive, or melting-type behavior. Additional flavorants, flavoring agents, additives, and other possible enhancing constituents are described in U.S. patent application Ser. No. 15/707,461 to Phillips et al., which is incorporated herein by reference in its entirety.

In addition to the inhalable substance (e.g., flavors, nicotine, or pharmaceuticals generally), the aerosol generating component may comprise one or more aerosol-forming or vapor-forming materials, such as a polyhydric alcohol (e.g., glycerin, propylene glycol, or a mixture thereof) and/or water. Representative types of aerosol forming materials are set forth in U.S. Pat. No. 4,793,365 to Sensabaugh, Jr. et al.; and U.S. Pat. No. 5,101,839 to Jakob et al.; PCT WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference. A preferred aerosol forming material produces a visible aerosol upon the application of sufficient heat thereto, and a highly preferred aerosol forming material produces an aerosol that can be considered to be "smoke-like." Further tobacco materials, such as a tobacco aroma oil, a tobacco essence, a spray dried tobacco extract, a freeze dried tobacco extract, tobacco dust, or the like may be combined with the vapor-forming or aerosol-forming material. It is also understood that the inhalable substance itself may be in a form whereby, upon heating, the inhalable substance is released as a vapor, aerosol, or combination thereof. In other implementations, the inhalable substance may not necessarily release in a vapor or aerosol form, but the vapor-forming or aerosol-forming material that may be combined therewith can form a vapor or aerosol upon heating and function essentially as a carrier for the inhalable substance itself. Thus, the inhalable substance may be characterized as being coated on a substrate, as being absorbed in a substrate, as being adsorbed onto a surface of a substrate, or as being a natural component of the substrate (i.e., the material forming the substrate, such as a tobacco or a tobacco-derived material). Likewise, an aerosol-forming or vapor-forming material may be similarly characterized. In certain implementations, the aerosol generating component may particularly comprise a substrate with the inhalable substance and a separate aerosol forming material included therewith. As such, in use, the substrate may be heated, the aerosol forming material may be volatilized into a vapor form taking with it the inhalable substance. In a specific example, the aerosol generating component may comprise a solid substrate with a slurry of tobacco and an aerosol-forming material and/or vapor-forming material coated thereon or absorbed or adsorbed therein. The substrate component may be any material that does not combust or otherwise degrade at the temperatures described herein that the heating member achieves to facilitate release of the inhalable substance. For example, a paper material may be used, including a tobacco paper (e.g., a paper-like material comprising tobacco fibers and/or reconstituted tobacco). Thus, in various implementations, the aerosol generating component may be characterized as comprising the inhalable substance, alternately as comprising the inhalable substance and a separate aerosol-former or vapor-former, alternately as comprising the inhalable substance and a substrate, or alternately as comprising the aerosol generating component, the separate aerosol-former or vapor-former, and the substrate. Thus, the substrate may contain one or both of the inhalable substance and the aerosol-former or vapor-former.

If desired, the tobacco material or the aerosol generating component may generally further include other components, such as sugars, glycerin, vanilla, cocoa, licorice, and other flavoring materials, such as menthol. Example plant-derived compositions that may be used are disclosed in U.S. Pat. App. Pub. No. 2012/0152265 to Dube et al., and U.S. Pat. No. 9,107,453 to Dube et al. The selection of such further components may vary based upon factors such as the sensory characteristics that are desired for the present article, and the present disclosure is intended to encompass any such further components that may be readily apparent to those skilled in the art of tobacco and tobacco-related or tobacco-derived products. See, Gutcho, *Tobacco Flavoring Substances and Methods*, Noyes Data Corp. (1972) and Leffingwell et al., *Tobacco Flavoring for Smoking Products* (1972).

The inhalable substance and/or the separate vapor forming material may be provided on the aerosol generating component in a variety of configurations. For example, both materials may be associated with the substrate such that the concentration of each material along the length of the substrate is substantially constant (e.g., when dividing the substrate into a plurality of lengthwise segments, the total concentration of material in each individual segment can be substantially similar, such as varying by less than 10%, less than 5%, or less than 2% by mass). In other implementations, one or both of the materials may be present in a defined pattern. For example, the pattern may be a gradient wherein the concentration continually increases or decreases along the length of the substrate. In this manner, the first puff on the article may provide an amount of the inhalable substance that is significantly greater than or less than the amount of the inhalable substance in the last puff. The gradient may also be designed to provide uniform production of inhalable substance across all puffs. Moreover, the pattern may be such that a bolus of inhalable substance is provided at some point along the length of the substrate (e.g., corresponding to the first puff, the last puff, or some intermediate puff on the article). Any variety of such patterns may be envisioned in light of the present disclosure, and such variations are likewise encompassed by the present disclosure. Such patterning likewise may apply to further components as described herein (e.g., flavorants). For example, a bolus of a flavorant may be provided on the substrate in a position to substantially correspond to the last puff or the last two or three puffs on the article. The release of such flavor may signal to the consumer that the final puff on the device is approaching or has been achieved. Various other configurations and components that may be included in the aerosol generating component of the present disclosure are described in in U.S. Pat. No. 9,078,473 to Worm et al., which is incorporated herein by reference in its entirety.

In some aspects of the present disclosure, the aerosol generating component may be configured as an extruded material, as described in U.S. Pat. App. Pub. No. 2012/0042885 to Stone et al., which is incorporated herein by reference in its entirety. In still other aspects, the aerosol generating component may be configured as an extruded structure and/or substrate that includes, or is essentially comprised of tobacco, tobacco-related material, glycerin, water, and/or a binder material, although certain formulations exclude the binder material. In various implementations, the binder material may be any binder material commonly used for tobacco formulations including, for example, carboxymethyl cellulose (CMC), gum (e.g. guar gum), xanthan, pullulan, and/or an alginate. According to some aspects, the binder material included in the aerosol delivery component may be configured to substantially maintain a structural shape and/or integrity of the aerosol delivery component. Various representative binders, binder properties, usages of binders, and amounts of binders are set forth in U.S. Pat. No. 4,924,887 to Raker et al., which is incorporated herein by reference in its entirety.

In some implementations, the aerosol generating component may be further configured to substantially maintain its structure throughout the aerosol-generating process. That is, the aerosol generating component is configured to substantially maintain its shape (i.e., the aerosol delivery component does not continually deform under an applied shear stress) throughout the aerosol-generating process. Although in some implementations the aerosol generating component may include liquids and/or some moisture content, in some implementations the aerosol generating component is configured to remain substantially solid throughout the aerosol-generating process and substantially maintain its structural integrity throughout the aerosol-generating process. Example tobacco and/or tobacco related materials suitable for a substantially solid aerosol delivery component are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are all incorporated herein in their entireties by reference respectively.

In yet another aspect, the aerosol generating component may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents.

In various implementations, the aerosol generating component wall may be formed substantially of a material that can include the inhalable substance naturally therein (e.g., tobacco paper) or may be formed of any further material (e.g., paper) that can have the inhalable substance and/or the vapor-former or aerosol-former entrained therein. In addition to the inhalable substance and/or the vapor-forming or aerosol-forming substance, the substrate wall may comprise additional components. For example, a vapor barrier may be included on the outer surface of the aerosol generating component wall. Preferably, the vapor barrier is positioned on the wall surface that is adjacent (or in contact with) the heating member when the aerosol generating component is heated. In particular implementations, the vapor barrier may be formed of a material that is electrical insulating or may comprise a layer of electrically insulating material that can be in contact with the heating member. For example, a metal foil may be used as the vapor barrier, and the foil may have an insulating monolayer—e.g., a metal oxide layer—in contact with the heating member to prevent release of vapor or aerosol into the exterior volume of the aerosol generating component and facilitate release of the vapor or aerosol into an annular space defined by the inner surface of the aerosol generating component wall. Any vapor barrier material, such as a metal foil, may be used.

In further implementations, the aerosol generating component may be formed of a material that softens or changes phase (especially from solid to molten) at about the working temperature of the article. For example, the aerosol generating component may be a wax or a gel, and the inhalable substance may be entrained therein. In such implementations, it can be particularly useful to include the vapor barrier (or similar material) that provides support to the aerosol generating component and substantially prevents the aerosol generating component from contacting the heating member. Likewise, the aerosol generating component may comprise a vapor barrier layer coated with an inhalable substance and/or an aerosol forming material. For example, one or more of such coating materials may be in a microencapsulated form that preferably releases its components at a temperature within one or more of the working ranges otherwise described herein. Microencapsulation technology that may be useful in such implementations is disclosed, for example, in U.S. Pat. No. 4,464,434 to Davis.

In one implementation, the aerosol generating component may comprise a tobacco component (such as, for example, a reconstituted cast tobacco sheet or tobacco beads) or a non-tobacco component (such as, for example, herbs, paper, cellulose, etc.) with one or more of the following: a binder component, a humectant component, a flavor component, a moisturizer component, and a casing material. In some implementations, the binder component may include, for example, cellulose and/or guar gum. In some implementations, the humectant component may comprise glycerol, for example at approximately 15-25%, sorbitol at approximately 14.5%, and/or propylene glycol at approximately 3-10%. In some implementations, the flavor component may comprise, for example, acetic acid, citric acid, acetoin, lactic acid, menthol, peppermint oil, carob bin/extract, cocoa products, licorice extract, invent sugar, and/or sucrose. In some implementations, the moisturizer component comprise, for example, water at approximately 15-25%.

As discussed above, the end of the aerosol source member 104 opposite the mouth end is sized and shaped for insertion into the receiving sleeve 116. In various implementations, the outer diameter (or other dimension depending upon the specific cross-sectional shape of the implementations) of the aerosol source member 104 is preferably sized to be slightly less than the inner diameter (or other dimension) of the receiving sleeve 116. Ideally, the difference in the respective diameters is sufficiently small so that the aerosol source member 104 fits snugly into the receiving sleeve 116, and frictional forces prevent the aerosol source member from being moved without an applied force.

As noted, in some implementations, the aerosol source member may include an overwrap. When the overwrap is present, the overall length thereof can vary from being substantially identical to the length of the aerosol generating component up to about two times the length of the aerosol generating component. Thus, the aerosol generating component may have a length that is up to about 50%, up to about 30%, or up to about 10% less than the length of the overwrap. Preferably, the aerosol generating component may have a length that is at least 10%, at least 15%, or at least 20% less than the length of the overwrap. More specifically, the distance the overwrap extends beyond the aerosol generating component may be about 5%, about 10%, about 15%, about 20%, about 25%, about 30%, about 40%, about 50%, about 60%, about 70%, about 80%, about 90%, or about 100% of the length of the aerosol generating component.

The overwrap also can function to provide particular characteristics at the mouth end of the aerosol source member. For example, the construction and/or shape and/or dimension of the overwrap can function to provide the sensation of a conventional cigarette in the mouth of a user.

Moreover, as noted the overwrap may comprise a filter (e.g., cellulose acetate or polypropylene) positioned in proximity to the mouth end of the cartridge to increase the structural integrity thereof and/or to provide filtering capacity, if desired, and/or to provide resistance to draw.

Figure 5:
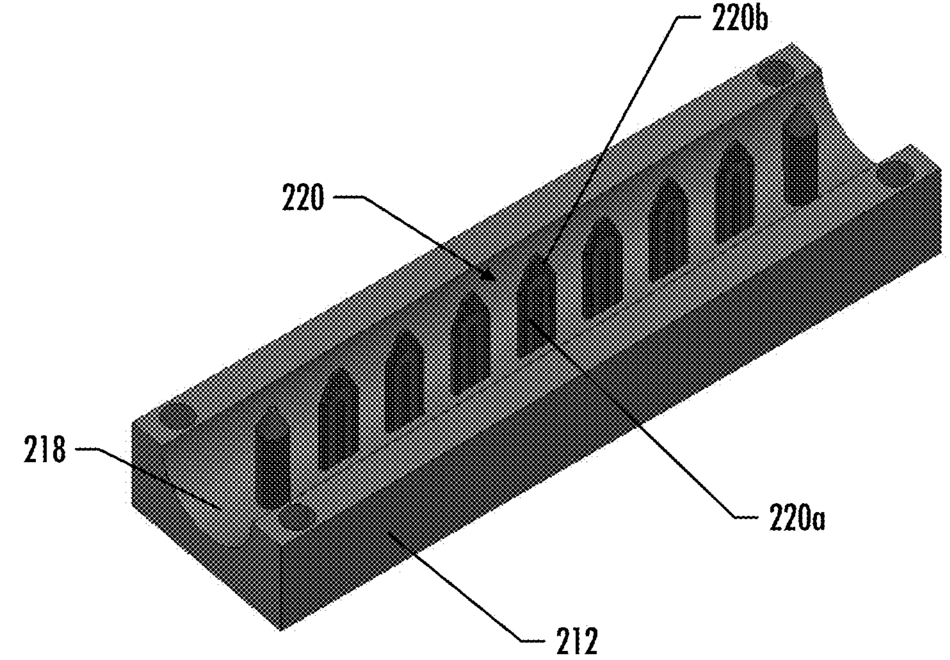
FIG. 5 illustrates a perspective view of a component of a heating assembly of an aerosol delivery device, in accordance with an example implementation of the present disclosure.

The implementations depicted in FIGS. 1-4 describe a heating assembly in which, in the closed position, a series of heating members (in these implementations the series of heating pins 120) pass through the aerosol source member 104. In other implementations, a series of heating members need not extend through the aerosol source member, but, rather, may extend some depth into an aerosol source member. For example, FIG. 5 illustrates a perspective view of a component of a heating assembly of an aerosol delivery device, in accordance with another example implementation of the present disclosure. In particular, FIG. 5 depicts a moveable jaw 212 that may be used in conjunction with a housing, electrical energy source, control component, and aerosol delivery device similar to those described above. Although in various implementations one or more of these components may differ (or may be omitted), reference is made to the descriptions above relating to these components.

Although other materials are possible, in the depicted implementation, the moveable jaw 212 may be made of a metal material (e.g., aluminum, stainless steel, metal alloys, etc.), a ceramic material (e.g., alumina, silica, mullite, silicon carbide, silicon nitride, aluminum nitride, boron nitride, etc.), a polymer material (e.g., polyimide, thermoplastic polyimide, polybenzimidazole, polyether ether ketone, polypropylene, high density polyethylene, etc.), a composite material, and/or any combinations thereof. As will be discussed in more detail below, the moveable jaw 212 of the depicted implementation is configured to move between an open position, in which the moveable jaw is spaced from a stationary jaw, and a closed position, in which the moveable jaw 212 is adjacent the stationary jaw. In many aspects, the moveable jaw 212 may be configured for use with a stationary jaw similar to the stationary jaw described with respect to FIGS. 1-4, and thus reference is made the description above; however, as will be explained in more detail below, the moveable jaw 212 of the depicted implementation is configured for use with a stationary jaw that need not include electrical connectors.

The moveable jaw 212 may be configured for use with a receiving sleeve similar to the receiving sleeve described with respect to FIGS. 1-4, and thus reference is made the description above. As similarly described above, the receiving sleeve of some implementations may have a substantially cylindrical shape configured to receive at least the heated end of the aerosol source member. In such implementations, each of the moveable jaw 212 and the stationary jaw may have an internal shape configured to substantially surround the receiving sleeve and thus at least the heated end of the aerosol source member. In particular, an interior surface 218 of the moveable jaw 112 and an interior surface of the stationary jaw together form a shape complementary of the shape of the receiving sleeve. In such a manner, when the moveable jaw 212 is in the closed position, the internal surfaces come together to surround the receiving sleeve.

The moveable jaw 212 of the depicted implementation includes a series of individual heating elements 220, which extend outward from the internal surface 218 thereof. The moveable jaw 212 of the depicted implementation also includes a pair of locating pins 222, which extend outward from the internal surface 218 of the moveable jaw 212, although it should be noted that in some implementations there need not be any locating pins 222. In the implementation described above with respect to FIGS. 1-4, a series of heating pins are configured to electrically connect (in the closed position) with a series of corresponding connectors located on a stationary jaw to create closed heating circuits; however, in the depicted implementation, the series of heating elements 220 comprise individual closed resistive heating circuits each of which is configured to heat a segment of the aerosol source member. As such, when the moveable jaw 212 is in in the closed position, the heating elements 220 extend some depth into the aerosol source member. For example, in some implementations, the heating elements 220 extend less than half-way through the aerosol source member. In other implementations, the heating elements 220 extend approximately half-way through the aerosol source member. In still other implementations, the heating elements 220 extend more than half-way through the aerosol source member. It should be noted that in some implementations, individual heating elements 220 within the series of heating elements 220 may extend different depths into the aerosol source member.

The heating elements 220 of the depicted implementation comprise resistive heating elements and have a blade-like shape (e.g., a relatively thin and flat configuration with an angled top portion), although in other implementations the heating elements 220 may have other shapes, such as, for example, a substantially cylindrical shape with a heating element positioned around an external surface thereof. Resistive heating elements may be configured to produce heat when an electrical current is directed therethrough. Such heating elements often comprise a metal material and are configured to produce heat as a result of the electrical resistance associated with passing an electrical current therethrough. In the depicted implementation, the heating elements include a heating element wire and/or trace **220*a* (hereinafter referred to as a "heating trace") that is constructed of an electrically resistant material. Examples of electrically resistive materials include, but are not limited to, titanium, silver, nickel, nichrome, stainless steel, tungsten, indium tin oxide, various metal alloys, ceramics such as silicon carbide and silicon nitride, composites, and/or any combination thereof. In various implementations, each heating trace 220*a* may be fixed on a main body portion 220*b* via various techniques including, for example, molding, printing, embedding, machining, squeeze casting, vapor deposition, etc. In various implementations, the main body portions 220*b* may be constructed of a metal material (e.g., aluminum, stainless steel, metal alloys, etc.). It should be noted that in other implementations, the main body 220*b*** may be constructed of another material, including, for example, a ceramic material (e.g., alumina, silica, mullite, silicon carbide, silicon nitride, aluminum nitride, oxides of metals such as zinc oxide, zirconium oxide, copper oxide, etc.), a polymer material (e.g., polyimide, thermoplastic polyimide, polybenzimidazole, polyether ether ketone, polypropylene, high density polyethylene, etc.) composite materials, and/or any combinations thereof.

As with the implementations described above with respect to FIGS. 1-4, the receiving sleeve of the depicted implementation is configured to receive the heated end of the aerosol source member, which may include an aerosol generating component. In the open position, the moveable jaw 212 is spaced from the stationary jaw, as well as the receiving sleeve and aerosol source member, and in the closed position, the moveable jaw 212 is adjacent the stationary jaw, with the receiving sleeve and aerosol source member disposed in between. In various implementations, actuation between the open position and the closed position (and vice versa) may be accomplished in a variety ways, including, for example, manually (e.g., a consumer may press the jaws together), or automatically or semi-automatically such as by using a hydraulic gas spring or other force-displacement mechanism that transfers directional force to the moveable jaw 212. Another example may include a linear displacement motor or other actuator configured to displace the moveable jaw 212 linearly between the open and closed positions. Other examples include a piezo actuator, an ultrasonic ceramic actuator, a rotating coil system, a lead screw system, and/or any other system configured for generating and transferring directional and/or rotational motion to the moveable jaw 212. Regardless of the mechanism, this motion may be activated via a pushbutton and/or via use of the device (such as, for example, by powering the device, by drawing on the aerosol source member, or by inserting an aerosol source member into the device) and/or via the electrical resistance probe method as similarly discussed above.

Figure 6:
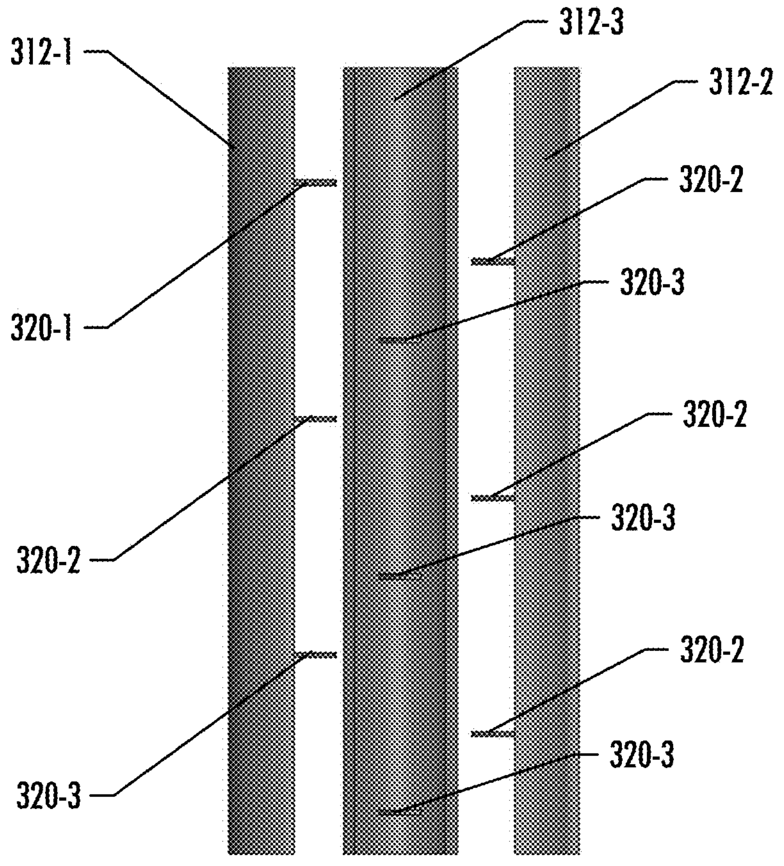
FIG. 6 illustrates top and perspective views of certain components of a heating assembly of an aerosol delivery device in an open position, in accordance with an example implementation of the present disclosure.
Figure 6:
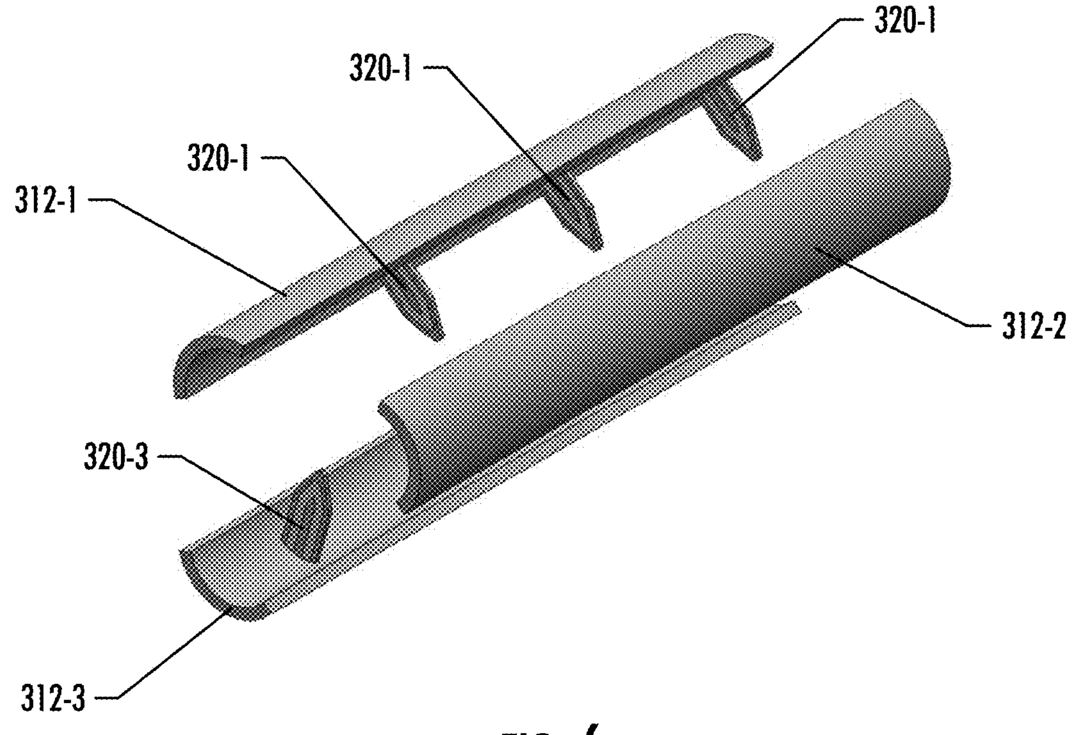
Figure 7:
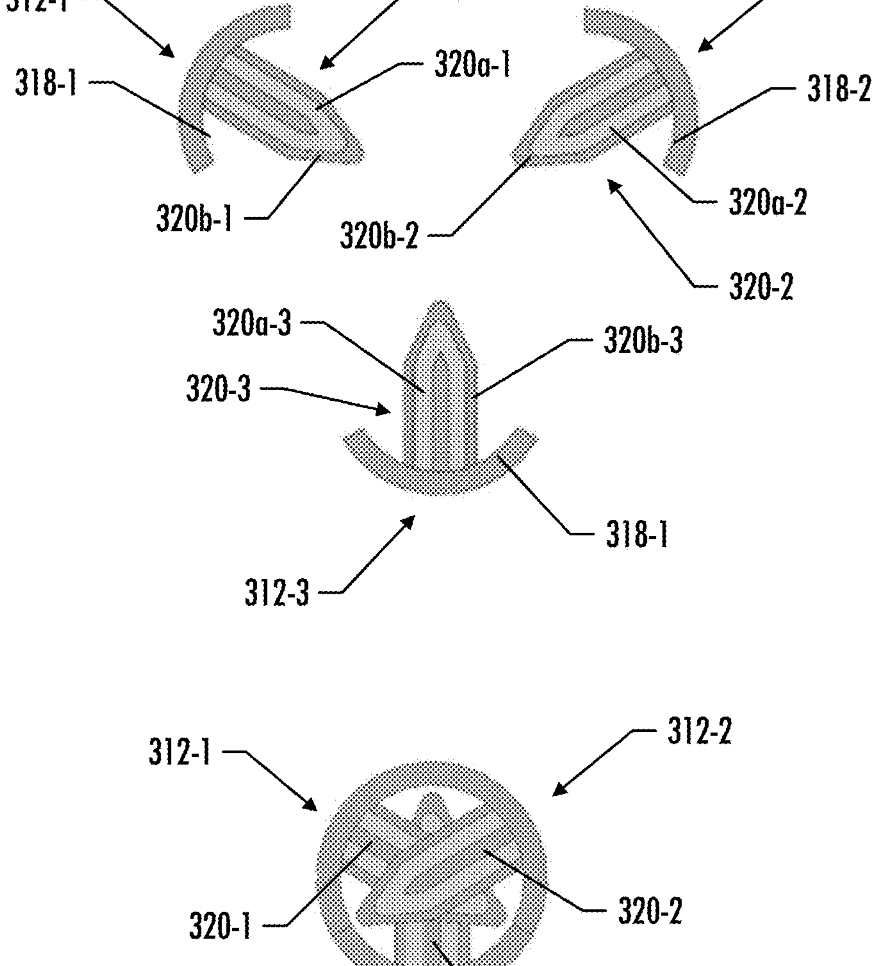
FIG. 7 illustrates a bottom view of certain components of a heating assembly of an aerosol source member shown in an open position and a closed position, in accordance with an example implementation of the present disclosure.

FIG. 6 illustrates top and perspective views of certain components of a heating assembly of an aerosol delivery device in an open position, according to another example implementation of the present disclosure, and FIG. 7 illustrates a bottom view of the components shown in an open position and a closed position. In particular, FIGS. 6 and 7 depicted a multi-piece moveable jaw 312 that may be used in conjunction with a housing, electrical energy source, control component, and aerosol delivery device similar to those described above. Although in various implementations one or more of these components may differ (or may be omitted), reference is made to the descriptions above relating to these components.

In various implementations, a multi-piece moveable jaw may include any number of sections, including, for example, as few as two sections, or as many as four or more sections. In the depicted implementation, the multi-piece moveable jaw 312 comprises three separate sections: a first movable jaw section 312-1, a second moveable jaw section 312-2, and a third moveable jaw section 312-3. Although other materials are possible, in the depicted implementation, the moveable jaw sections 312-1, 312-2, 312-3 may be made of any of the following materials: metal materials (e.g., aluminum, stainless steel, metal alloys, etc.), ceramic materials (e.g., alumina, silica, mullite, silicon carbide, silicon nitride, aluminum nitride, etc.), polymers (e.g., polyimide, thermoplastic polyimide, polybenzimidazole, polyether ether ketone, polypropylene, high density polyethylene, etc.) composite materials, and/or any combinations thereof. As will be discussed in more detail below, the moveable jaw sections 312-1, 312-2, 312-3 are configured to move together between an open position, in which the moveable jaw sections 312-1, 312-2, 312-3 are spaced from each other, and a closed position, in which the moveable jaw sections 312-1, 312-2, 312-3 are adjacent each other. In the depicted implementation, there need not be a stationary jaw, as the configuration of the moveable jaw sections 312-1, 312-2, 312-3 in a closed position create a substantially closed form that surrounds the aerosol source member (and receiving sleeve, which may be included in some implementations).

As similarly described above, the receiving sleeve of some implementations may have a substantially cylindrical shape configured to receive at least the heated end of the aerosol source member. In such implementations, the moveable jaw sections 312-1, 312-2, 312-3 may have an internal shape configured to substantially surround the receiving sleeve and thus at least the heated end of the aerosol source member. In particular, the interior surfaces 318-1, 318-2, 318-3 of the moveable jaw sections 312-1, 312-2, 312-3 together form a shape complementary of the shape of the receiving sleeve. In such a manner, when the moveable jaw sections 312-1, 312-2, 312-3 are in the closed position, the internal surfaces come together to surround the receiving sleeve.

Each moveable jaw section 312-1, 312-2, 312-3 of the depicted implementation includes a series of heating elements 320-1, 320-2, 312-3, which extend outward from respective internal surfaces 318-1, 318-2, 318-3 thereof. In other implementations, it will be appreciated that additional or fewer heating elements may be included on each movable jaw section. For example, in one implementation, a single heating element may be included on each of moveable jaw sections such that there are a total of three heating elements. Although other implementations may differ (referring to the top view shown in FIG. 6), the series of heating elements 320-1, 320-2, 312-3 of the depicted implementation have a staggered configuration such that individual heating elements of the series of heating elements 20-1, 320-2, 312-3 do not align with each other, and thus overlap when the moveable jaw sections 312-1, 312-2, 312-3 are in the closed position. In the depicted implementation, each of the series of heating elements 320-1, 320-2, 312-3 comprises individual closed resistive heating circuits, which are configured to heat a segment of the aerosol source member. As such, when the moveable jaw sections 312-1, 312-2, 312-3 are in in the closed position, the heating elements 320-1, 320-2, 320-3 extend some depth into the aerosol source member. For example, in the depicted implementation, the heating elements 320-1, 320-2, 320-3 extend more than half-way through the aerosol source member. However, in other implementations, the heating elements 320-1, 320-2, 320-3 may extend approximately half-way through the aerosol source member, and in still other implementations the heating elements 320-1, 320-2, 320-3 may extend less than half-way through the aerosol source member.

The heating elements 320-1, 320-2, 320-3 of the depicted implementation comprise resistive heating elements and have a blade-like shape, although in other implementations the heating elements 320-1, 320-2, 320-3 may have other shapes. Resistive heating elements may be configured to produce heat when an electrical current is directed therethrough. Such heating elements often comprise a metal material and are configured to produce heat as a result of the electrical resistance associated with passing an electrical current therethrough. Referring to FIG. 7, each of the heating elements 320-1, 320-2, 320-3 includes a heating element trace **320*a*-1, 320*a*-2, 320*a*-3 that is constructed of an electrically resistant material. Examples of electrically resistive materials include, but are not limited to, titanium, silver, nickel, nichrome, stainless steel, indium tin oxide, various metal alloys, ceramics such as silicon carbide and silicon nitride, composites, and/or any combination thereof. In various implementations, the heating traces 320*a*-1, 320*a*-2, and 320*a*-3 may be fixed on the main body 320*b*-1, 320*b*-2, 320*b*-3 via printing, embedding, machining, squeeze casting, etc. In various implementations, the heating trace may be fixed on a main body 320*b*-1, 320*b*-2, 320*b*-3 that is constructed of a metal material (e.g., aluminum, stainless steel, metal alloys, etc.). It should be noted that in other implementations, the main body 220*b*** may be constructed of another material, including, for example, a ceramic material (e.g., alumina, silica, mullite, silicon carbide, silicon nitride, aluminum nitride, etc.), a polymer material (e.g., polyimide, thermoplastic polyimide, polybenzimidazole, polyether ether ketone, polypropylene, high density polyethylene, etc.) composite materials, and/or any combinations thereof.

Although in other implementations there may not be a receiving sleeve, in the depicted implementation, a receiving sleeve (not shown) may be configured to receive the heated end of the aerosol source member. In the open position, the moveable jaw sections 312-1, 312-2, 312-3 are spaced from each other, as well as the receiving sleeve and aerosol source member. In the closed position, the moveable jaw sections 312-1, 312-2, 312-3 are adjacent each other, with the receiving sleeve and aerosol source member disposed in between. In various implementations, actuation between the open position and the closed position (and vice versa) may be accomplished in a variety ways, including, for example, manually (e.g., a consumer may press the jaws together), or automatically or semi-automatically such as by using a hydraulic gas spring or other force-displacement mechanism that transfers directional force to the moveable jaw 312-1, 312-2, 312-3. Another example may include a linear displacement motor or other actuator configured to displace the moveable jaw sections 312-1, 312-2, 312-3 between the open and closed positions. Other examples include a piezo actuator, an ultrasonic ceramic actuator, a rotating coil system, a lead screw system, a cam follower mechanism, a gear mechanism, a linkage, and/or any other system configured for generating and transferring directional and/or rotational motion to the moveable jaw sections 312-1, 312-2, 312-3. Regardless of the mechanism, this motion may be activated via a pushbutton and/or via use of the device (such as, for example, by powering the device, by drawing on the aerosol source member, or by inserting an aerosol source member into the device) and/or via the electrical resistance probe method as similarly discussed above.

Figure 8:
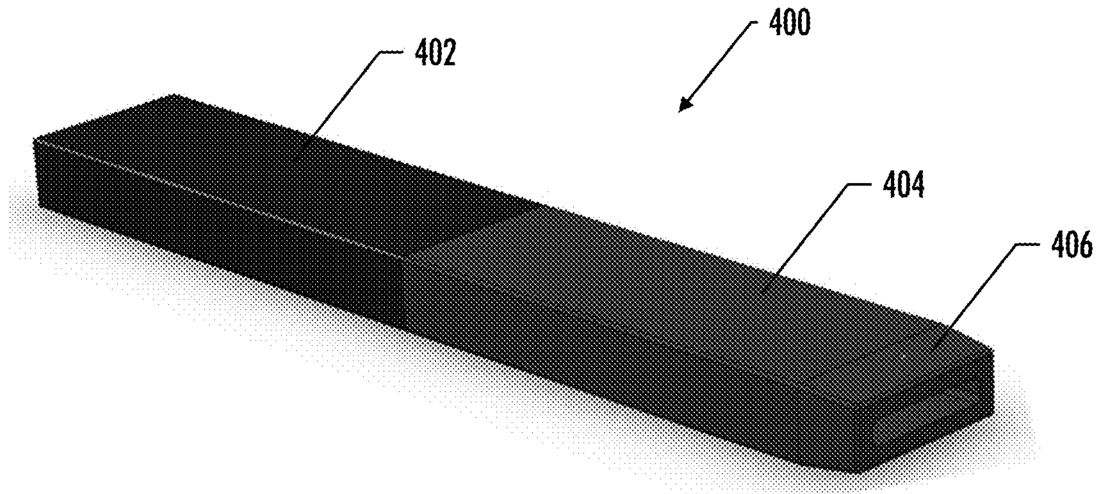
FIG. 8 illustrates a perspective view of an aerosol delivery device, in accordance with an example implementation of the present disclosure.
Figure 9:
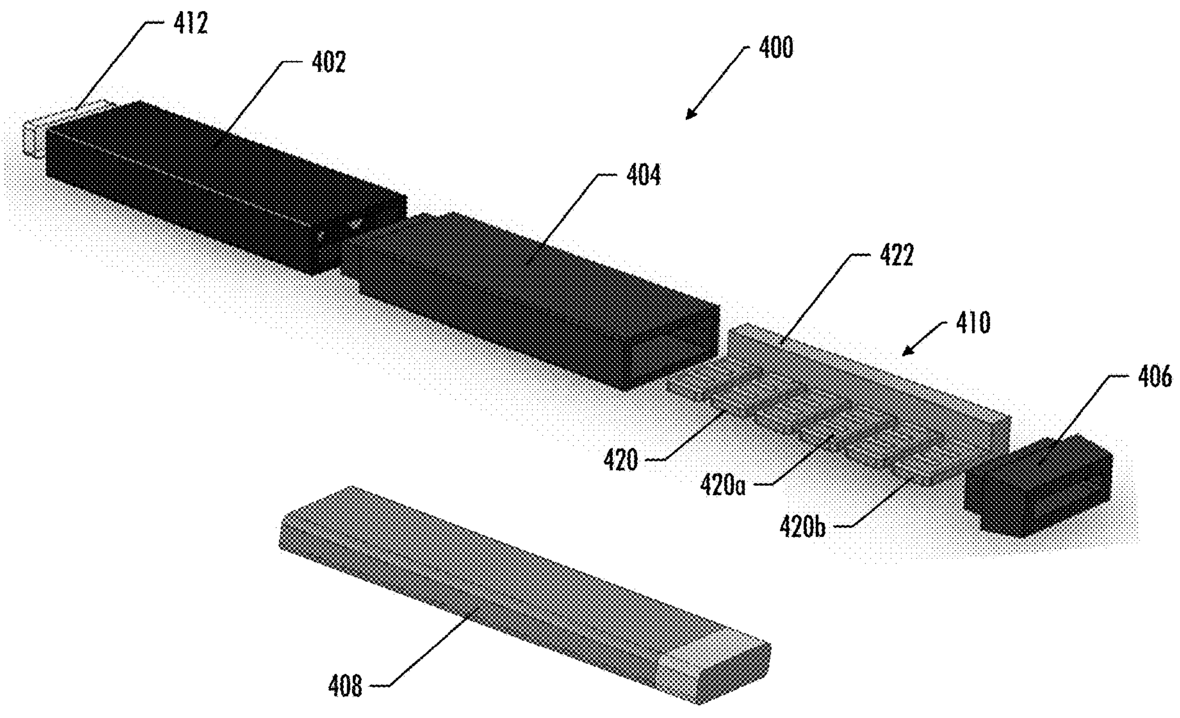
FIG. 9 illustrates a perspective exploded view of an aerosol delivery device, in accordance with an example implementation of the present disclosure.

FIG. 8 illustrates a perspective view of an aerosol delivery device 400, in accordance with another example implementation of the present disclosure, and FIG. 9 illustrates a perspective exploded view of the aerosol delivery device 400. In particular, the aerosol delivery device 400 of the depicted implementation includes a first housing portion 402, a second housing portion 404, a mouthpiece 406, an aerosol source member 408 (that includes an aerosol generating component, an overwrap, and a filter), a heating assembly 410, and an indicator 412. The aerosol delivery device 400 further includes an electrical energy source (not visible, e.g., a battery, which may be rechargeable, and/or a rechargeable supercapacitor), and a control component, (not visible, e.g., a microprocessor, individually or as part of a microcontroller, a printed circuit board (PCB) that includes a microprocessor and/or microcontroller, etc.). As will be discussed in more detail below, the heating assembly 410 of various implementations comprises a series of independent and distinct heating members, wherein each heating member is configured to heat a segment of the aerosol source member 408.

In various implementations, one or both of the control component and the electrical energy source may be coupled with the first housing portion 402 and/or the second housing portion 404. For the sake of the current application, the phrase "coupled with" when used with respect to one component relative to another may encompass implementations in which one component is located within another component and/or implementations wherein one component is separate but otherwise operatively connected to another component. For example, in the depicted implementation, both the control component and the electrical energy source are located within the first housing portion 402; however, in other implementations one or both of the control component and the electrical energy source may be located in different components. Further information regarding the control component and the electrical energy source is provided below.

In various implementations, the first housing portion 402 and the second housing portion 404 may be mechanically engaged together in a variety of ways. For example, in some implementations, the first housing portion 402 and the second housing portion 404 may engage via a threaded connection. In other implementations, the first housing portion 402 and the second housing portion 404 may engage via an interference or friction fit. In other implementations, the first housing portion 402 and the second housing portion 404 may engage via a magnetic connection. In other implementations, the first housing portion 402 and the second housing portion 404, may engage via a snap fit connection. In still other implementations, the first housing portion 402 and the second housing portion 404 engage via a bayonet-type connection that includes a male component (e.g., a pin) and a female component (e.g., an L-shaped slot). It should be noted that in some implementations, the first housing portion 402 and the second housing portion 404 may comprise a single, unitary housing portion.

Although other implementations may differ, in the depicted implementation the aerosol source member 408 is inserted into the second housing portion 404 by removing the mouthpiece 406 and inserting the aerosol source member 408 so that it is positioned proximate (e.g., over) the heating assembly 410. In the depicted implementation, there is a single series of heating elements 420 that extend from the heating assembly frame 422 such that they are configured to be positioned on one side of the aerosol source member 408; however, in other implementations there may be two or more series of heating elements 420 that are configured to be positioned on opposite sides of the aerosol source member 408. After insertion of the aerosol source member 408, the mouthpiece 406 can then be reinserted into the second housing portion 404 such that the filter end of aerosol source member 404 is closest to the mouthpiece 406. In such a manner, one or both the second housing portion 404 or the aerosol source member 408 may be keyed or otherwise may include a stopping or locating feature to facilitate proper positioning thereof. In various implementations, the first housing portion 402, the second housing 404, and/or the mouthpiece 406 may be detachable from each other, and thus any one or all may be replaceable.

In some implementations, the first housing portion 402 and/or the second housing portion 404 may also include one or more pushbuttons configured to activate certain operations of the device 400, such as, for example, turning on the device and initiating heating of the heating assembly 410 (e.g., one or more heating elements of the heating assembly). As will be discussed in more detail below, in various implementations, the aerosol source member 408 may comprise an aerosol generating component, which is configured to be located proximate the heating assembly 410, and a filter, which is configured to be located proximate the mouthpiece 406. It should be noted that while the first housing portion 402, the second housing portion 404, and the aerosol source member 408 of the depicted implementation have a substantially elongate rectangular cuboid shape, in other implementations the first housing portion 402, the second housing portion 404, and/or the aerosol source member 408 may have any other shape, including, for example, the shape of a conventional cigarette or cigar.

In specific implementations, the first housing portion 402, the second housing portion 404, and/or the aerosol source member 408 may be referred to as being disposable or as being reusable. For example, the electrical energy source and/or the first housing portion 402 containing the electrical energy source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 408 and/or the second housing portion 404 containing the aerosol source member, and/or the mouthpiece 406 may comprise a single-use device. A single use component for use with a control body is disclosed in U.S. Pat. No. 8,910,639 to Chang et al., which is incorporated herein by reference in its entirety.

In various implementations, the control component may comprise a control circuit (which may be connected to further components, as further described herein) that may be connected by electrically conductive wires to the electrical energy source. In various implementations, the control component may control when and how the heating assembly 410 (e.g., one or more heating members of the heating assembly) receives electrical energy to heat the aerosol generating component for release of the inhalable substance for inhalation by a consumer. Such control (e.g., control of the stage of heating, including preheating and final heating) can relate to actuation of pressure sensitive switches or the like, which are described in greater detail hereinafter. It should be noted that the terms "connected" or "coupled" should not be read as necessitating direct connection without an intervening component. Rather, these terms may encompass direct connection and/or connection via one or more intervening components. As such, in various implementations these terms may be understood to mean operatively connected to or operatively coupled with. In various implementations, the control component of the present disclosure may comprise the control component described in U.S. patent application Ser. No. 15/976,526, filed on May 10, 2018, and titled Control Component for Segmented Heating in an Aerosol Delivery Device, which is incorporated herein by reference in its entirety.

In various implementations, the control component may also be configured to closely control the amount of heat provided to the aerosol generating component of the aerosol source member. While the heat needed to volatilize the aerosol generating component in a sufficient volume to provide a desired dosing of the inhalable substance for a single puff can vary for each particular substance used, it can be particularly useful for the heating member to heat to a temperature of at least 120° C., at least 130° C., or at least 140° C. In some imlementations, pre-heating may occur at least 50° C., at least 75° C., at least 100° C., or 125° C. In some implementations, in order to volatilize an appropriate amount of the aerosol generating component and thus provide a desired dosing of the inhalable substance, the heating temperature may be at least 150° C., at least 200° C., at least 250° C., at least 300° C., or at least 350° C. It can be particularly desirable, however, to avoid heating to temperatures substantially in excess of about 550° C. in order to avoid degradation and/or excessive, premature volatilization of the aerosol generating component. Heating specifically should be at a sufficiently low temperature and sufficiently short time so as to avoid significant combustion (preferably any combustion) of the aerosol generating component. The present disclosure may particularly provide the components of the present article in combinations and modes of use that will yield the inhalable substance in desired amounts at relatively low temperatures. As such, yielding can refer to one or both of generation of the aerosol within the article and delivery out of the article to a consumer. In specific implementations, the heating temperature may be about 120° C. to about 300° C., about 130° C. to about 290° C., about 140° C. to about 280° C., about 150° C. to about 250° C., or about 160° C. to about 200° C. The duration of heating can be controlled by a number of factors, as discussed in greater detail hereinbelow. Heating temperature and duration may depend upon the desired volume of aerosol and ambient air that is desired to be drawn through the aerosol source member, as further described herein. The duration, however, may be varied depending upon the heating rate of the heating members, as the article may be configured such that the heating members are energized only until a desired temperature is reached. Alternatively, duration of heating may be correlated with the duration of a puff on the article by a consumer. Generally, the temperature and time of heating (as well as the energizing turn of the heaters) will be controlled by one or more components contained in the control body, as noted above.

The amount of inhalable material released by the aerosol source member can vary based upon the nature of the aerosol forming component. Preferably, the aerosol source member is configured with a sufficient amount of the aerosol forming component, with a sufficient amount of any aerosol-former, and to function at a sufficient temperature for a sufficient time to release a desired amount over a course of use. The amount may be provided in a single inhalation from the aerosol source member or may be divided so as to be provided through a number of puffs from the article over a relatively short length of time (e.g., less than 30 minutes, less than 20 minutes, less than 15 minutes, less than 10 minutes, or less than 5 minutes). For example, the device may provide nicotine in an amount of about 0.01 mg to about 0.1 mg, about 0.05 mg to about 1.0 mg, about 0.08 mg to about 0.5 mg, about 0.1 mg to about 0.3 mg, or about 0.15 mg to about 0.25 mg per puff on the aerosol source member. In other implementations, a desired amount may be characterized in relation to the amount of wet total particulate matter delivered based on puff duration and volume. For example, the aerosol source member may deliver at least 1.0 mg of wet total particulate matter on each puff, for a defined number of puffs (as otherwise described herein), when smoked under standard FTC smoking conditions of 2 second, 35 ml puffs. Such testing may be carried out using any standard smoking machine. In other implementations, the amount of total particulate matter (TPM) yielded under the same conditions on each puff may be at least 1.5 mg, at least 1.7 mg, at least 2.0 mg, at least 2.5 mg, at least 3.0 mg, about 1.0 mg to about 5.0 mg, about 1.5 mg to about 4.0 mg, about 2.0 mg to about 4.0 mg, about 2.0 mg to about 3.0 mg, about 4.0 mg to about 6.0 mg, about 6.0 mg to about 8.0 mg, or about 8.0 mg to about 10.0 mg.

As noted, the aerosol delivery device 400 of some implementations may include a pushbutton, which may be linked to the control component for manual control of the heating members. For example, in some implementations the consumer may use the pushbutton to energize the heating assembly 410. Similar functionality tied to the pushbutton may be achieved by other mechanical means or non-mechanical means (e.g., magnetic or electromagnetic). Thusly, activation of the heating assembly 410 may be controlled by a single pushbutton. Alternatively, multiple pushbuttons may be provided to control various actions separately. In some implementations, one or more pushbuttons present may be substantially flush with the casing of the first housing portion 402 and/or the second housing portion 404.

Instead of (or in addition to) any pushbuttons, the aerosol delivery device 400 of the present disclosure may include components that energize the heating assembly 410 in response to the consumer's drawing on the article (i.e., puff-actuated heating). For example, the device may include a switch or flow sensor (not shown) in the first housing portion 402, and/or the second housing portion 404, and/or the mouthpiece 406 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch, or a touch sensor (e.g., capacitive touch sensor) configured to sense contact between a user (e.g., mouth or fingers of user) and one or more surfaces of the aerosol delivery device 400. An example mechanism that can provide such puff-actuation capability includes a Model 163PC01D36 silicon sensor, manufactured by the MicroSwitch division of Honeywell, Inc., Freeport, Ill. With such sensor, the heating assembly 410 may be activated rapidly by a change in pressure when the consumer draws on the device. In addition, flow sensing devices, such as those using hot-wire anemometry principles, may be used to cause the energizing of the heating assembly sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and aerosol source member may be included in the first housing portion 402 and/or the second housing portion 404 so that pressure changes during draw are readily identified by the switch. Other example puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In some implementations, when the consumer draws on the mouthpiece 406, the current actuation means may permit unrestricted or uninterrupted flow of current through the heating assembly 410 to generate heat rapidly. Because of the rapid heating, it can be useful to include current regulating components to (i) regulate current flow through the heating members to control heating of the resistance element and the temperature experienced thereby, and (ii) prevent overheating and degradation of the aerosol generating component. In some implementations, the current regulating circuit may be time-based. Specifically, such a circuit may include a means for permitting uninterrupted current flow through the heating members for an initial time period during draw, and a timer means for subsequently regulating current flow until draw is completed. For example, the subsequent regulation can include the rapid on-off switching of current flow (e.g., on the order of about every 1 to 50 milliseconds) to maintain the heating members within the desired temperature range. Further, regulation may comprise simply allowing uninterrupted current flow until the desired temperature is achieved then turning off the current flow completely. The heating members may be reactivated by the consumer initiating another puff on the article (or manually actuating the pushbutton, depending upon the specific switch implementation employed for activating the heater). Alternatively, the subsequent regulation can involve the modulation of current flow through the heating members to maintain the heating members within a desired temperature range. In some implementations, so as to release the desired dosing of the inhalable substance, the heating members may be energized for a duration of about 0.2 second to about 5.0 seconds, about 0.3 second to about 4.0 seconds, about 0.4 second to about 3.0 seconds, about 0.5 second to about 2.0 seconds, or about 0.6 second to about 1.5 seconds. One example time-based current regulating circuit can include a transistor, a timer, a comparator, and a capacitor. Suitable transistors, timers, comparators, and capacitors are commercially available and will be apparent to the skilled artisan. Example timers are those available from NEC Electronics as C-1555C and from General Electric Intersil, Inc. as ICM7555, as well as various other sizes and configurations of so-called "555 Timers". An example comparator is available from National Semiconductor as LM311. Further description of such time-based current regulating circuits is provided in U.S. Pat. No. 4,947,874 to Brooks et al., which is incorporated herein by reference in its entirety.

In some implementations, the order of energizing of the heaters may be controlled by the control component and corresponding data may be recorded such that if a user turns off the device (without replacing the aerosol source member), the user may be able to later turn on the device and continue consuming the remaining portion of the aerosol source member. For example, if the first two heaters have been energized and the corresponding portions of the aerosol source member have been consumed by consumer, the user may turn off the device, and when the user turns the device back on, the device will start with the third heater. As such, in some implementations aerosol source member consumption status data may be reset when an aerosol source member is removed from the device. In some implementations, individual heaters may be programmed to be energized for a number of puffs (e.g., one to five puffs, or more) before the next heater is energized. In various implementations, such programming may depend on the number of total heaters, the consumable type and/or features (e.g., mass, size, glycerol level, etc.). In light of the foregoing, it can be seen that a variety of mechanisms can be employed to facilitate actuation/deactuation of current to the heating members. For example, the device may include a timer for regulating current flow in the article (such as during draw by a consumer). The device may further include a timer responsive switch that enables and disables current flow to the heating members. Current flow regulation also can comprise use of a capacitor and components for charging and discharging the capacitor at a defined rate (e.g., a rate that approximates a rate at which the heating member heats and cools). Current flow specifically may be regulated such that there is uninterrupted current flow through the heating members for an initial time period during draw, but the current flow may be turned off or cycled alternately off and on after the initial time period until draw is completed. Such cycling may be controlled by a timer, as discussed above, which can generate a preset switching cycle. In specific implementations, the timer may generate a periodic digital wave form. The flow during the initial time period further may be regulated by use of a comparator that compares a first voltage at a first input to a threshold voltage at a threshold input and generates an output signal when the first voltage is equal to the threshold voltage, which enables the timer. Such implementations further can include components for generating the threshold voltage at the threshold input and components for generating the threshold voltage at the first input upon passage of the initial time period.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties. Another method uses an electrical resistance change for actuating the aerosol delivery device and/or the heating assembly thereof. It works by using a very thin small metallic probe in the form of strip or wire that is installed perpendicular to the air flow inside the cartridge. The air flow generated by the user applies mechanical force on the probe and folds it to some extent. Due to this change in geometry that results in bending/tension in part of the probe, a change in electrical resistance of the probe occurs, this resistance alteration is sent as a pulse/information to the PCB and works as a trigger to activate the heating assembly 410.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. patent application Ser. No. 14/881,392 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

As noted above, the electrical energy source used to provide power to the various electrical components of the device 400 may take on various implementations. Preferably, the electrical energy source is able to deliver sufficient energy to rapidly heat the heating members in the manner described above and power the device through use with multiple aerosol source members 408 while still fitting conveniently in the device 400. Examples of useful electrical energy sources include lithium-ion batteries that are preferably rechargeable (e.g., a rechargeable lithium-manganese dioxide battery). In particular, lithium polymer batteries can be used as such batteries can provide increased safety. Other types of batteries—e.g., nickel-cadmium cells—may also be used. Additionally, a preferred electrical energy source is of a sufficiently light weight to not detract from a desirable smoking experience. Some examples of possible electrical energy sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

One example of an electrical energy source is a TKI-1550 rechargeable lithium-ion battery produced by Tadiran Batteries GmbH of Germany. In another implementation, a useful electrical energy source may be a N50-AAA CAD- NICA nickel-cadmium cell produced by Sanyo Electric Company, Ltd., of Japan. In other implementations, a plurality of such batteries, for example providing 1.2-volts each, may be connected in series. Other electrical energy sources, such as rechargeable lithium-manganese dioxide batteries, may also be used. Any of these batteries or combinations thereof may be used in the electrical energy source, but rechargeable batteries are preferred because of cost and disposal considerations associated with disposable batteries. In implementations where rechargeable batteries are used, the aerosol delivery device 400 may further include charging contacts for interaction with corresponding contacts in a conventional recharging unit (not shown) deriving power from a standard 120-volt AC wall outlet, or other sources such as an automobile electrical system or a separate portable power supply. In further implementations, the electrical energy source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the device 400. Thus, the present disclosure also may include a charger component that can be attached to the device between uses to replenish the supercapacitor. Thin film batteries may be used in certain implementations of the present disclosure.

As noted above, in various implementations, the aerosol delivery device 400 may comprise one or more indicators, such as indicator 412, which in the depicted implementation is located proximate a distal end of the first housing portion 402. In various implementations, the one or more indicators may be located at any location on the first housing portion 402, and/or the second housing portion 404, and/or the mouthpiece 406. In some implementations, an indicator may comprise a light (e.g., a single or multi-color light emitting diode (LED)) that may provide indication of multiple aspects of use of the device. For example, in some implementations a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In other implementations, for example, each light may correspond to a respective heating element and once a respective heating element has reached a puff threshold (e.g., one to five puffs or more), the light may be turned off, indicating that part of the aerosol source member is spent. In still other implementations, only a single indicator may be present, and lighting thereof may indicate that current was flowing to the heating member and the device is actively heating. This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In various implementations, the first housing portion 402, and/or the second housing portion 404, and/or the mouthpiece 406 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as further discussed herein. In some implementations, a heat resistant polymer may be used. In other implementations, ceramic materials may be used. In further implementations, an insulating material may be used so as not to unnecessarily move heat away from the aerosol source member. The housing, when formed of a single layer, may have a thickness that preferably is about 0.1 mm to about 2 mm, about 0.2 mm to about 5.0 mm, about 0.5 mm to about 4.0 mm, about 0.5 mm to about 3.0 mm, or about 1.0 mm to about 3.0 mm. Further example types of components and materials that may be used to provide the functions described above or be used as alternatives to the materials and components noted above can be those of the types set forth in U.S. Pat. App. Pub. Nos. 2010/00186757 to Crooks et al.; 2010/00186757 to Crooks et al.; and 2011/0041861 to Sebastian et al.; the disclosures of the documents being incorporated herein by reference in their entireties.

As shown in FIG. 9, the depicted implementation includes a heating assembly 410 that includes a series of individual resistive heating elements 420 that extend from a heating assembly frame 422. In various implementations, the control component is configured to control the individual heating elements 420 independently and/or in any combination, with activation of the heating elements 420 being initiated using any of the methods described above. In the depicted implementation, each of the heating elements 420 is configured to heat a segment of the aerosol source member 408. The heating elements 420 of the depicted implementation comprise resistive heating elements and have a substantially planar rectangular shape, although in other implementations the heating elements 420 may have other shapes. Resistive heating elements may be configured to produce heat when an electrical current is directed therethrough. Such heating elements often comprise a metal material or an electrically conductive ceramic material and are configured to produce heat as a result of the electrical resistance associated with passing an electrical current therethrough. In the depicted implementation, each of the heating elements includes a heating element wire and/or trace 420*a* (hereinafter referred to as a "heating trace") that is constructed of an electrically resistant material. Examples of electrically resistive materials include, but are not limited to, titanium, silver, nickel, nichrome, stainless steel, tungsten, indium tin oxide, various metal alloys, ceramics such as silicon carbide and silicon nitride, composites, and/or any combination thereof. In various implementations, each heating trace 420*a* may be fixed on a main body portion 420*b*, which in the depicted implementation may be an extension of, or part of, the heating assembly frame 422. In various implementations, each heating trace 420*a* may be created on a corresponding main body portion 420*b* via printing, embedding, machining, squeeze casting, and other particle deposition techniques, such as chemical vapor deposition (CVD), physical vapor deposition (PVD), etc. In various implementations, the heating assembly frame 422 and/or the main body portion 420*b* may be constructed of a metal material (e.g., aluminum, stainless steel, metal alloys, etc.); however, in other implementations, the heating assembly frame 422 and/or the main body 420*b* may be constructed of another material, including, for example, a ceramic material (e.g., alumina, silica, mullite, silicon carbide, silicon nitride, aluminum nitride, boron nitride, etc.), a polymer material (e.g., polyimide, thermoplastic polyimide, polybenzimidazole, polyether ether ketone, polypropylene, high density polyethylene, etc.) composite materials, and/or any combinations thereof.

Figure 10:
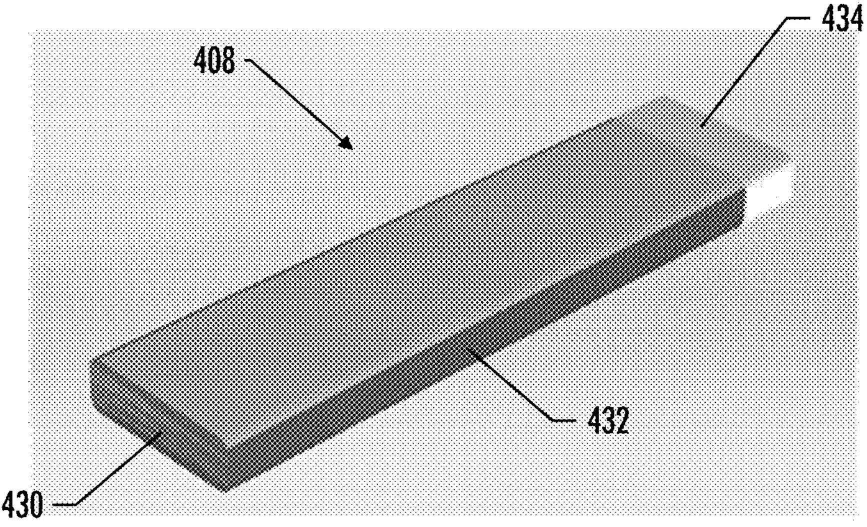
FIG. 10 illustrates a perspective view of an aerosol source member, in accordance with an example implementation of the present disclosure.

FIG. 10 illustrates a perspective view of the aerosol source member 408 of FIG. 9, in accordance with an example implementation of the present disclosure. In the depicted implementation, the aerosol source member 408 includes an aerosol generating component 430, an overwrap material 432, and a filter 434. As will be discussed in more detail below, when the aerosol source member 408 of the depicted implementation is installed into the second housing portion 404 of the aerosol delivery device 400, the filter 434 may be positioned proximate the mouthpiece 406. In some implementations, the aerosol source member 408 may be insertable and removable from the second housing portion 404 such as, for example, by removing the mouthpiece 406. In other implementations, the second housing portion 404 and the aerosol source member 408 may be insertable and removable from the first housing portion 402.

As noted, the aerosol generating component 430 of the depicted implementation may comprise a solid or semi-solid material that may be a tobacco or tobacco-derived material or a non-tobacco material. In various implementations, such a material may comprise tobacco-containing beads, tobacco shreds, tobacco strips, reconstituted tobacco material, or combinations thereof, and/or a mix of finely ground tobacco, tobacco extract, spray dried tobacco extract, extruded tobacco, tobacco caste sheet, or other tobacco form mixed with optional inorganic materials (such as calcium carbonate), optional flavors and/or binders, and aerosol forming materials, such as, for example, glycerol, to form a substantially solid or moldable (e.g., extrudable) substrate. Gels and suspensions may also be utilized. Some representative types of solid and semi-solid aerosol generating component constructions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein in their entireties.

As noted above, in various implementations, the aerosol generating component may include an aerosol generating component. The aerosol generating component may be any material that, when heated, releases an inhalable substance, such as a flavor-containing substance. In the implementation depicted in the figures, the aerosol generating component is a solid or semi-solid substrate comprising the inhalable substance. The inhalable substance specifically may be a tobacco component or a tobacco-derived material (i.e., a material that is found naturally in tobacco that may be isolated directly from the tobacco or synthetically prepared) or a non-tobacco material. For example, the aerosol generating component may comprise tobacco extracts or fractions thereof combined with an inert substrate. The aerosol generating component may further comprise unburned tobacco or a composition containing unburned tobacco that, when heated to a temperature below its combustion temperature, releases an inhalable substance. Although less preferred, the aerosol generating component may comprise tobacco condensates or fractions thereof (i.e., condensed components of the smoke produced by the combustion of tobacco, leaving flavors and, possibly, nicotine).

In various implementations, heating of the aerosol generating component 430 may result in aerosolization of an aerosol precursor composition associated with the aerosol generating component 430. In various implementations, the filter 434 of the aerosol source member 408 may be configured to receive the generated aerosol therethrough in response to a draw applied to the mouthpiece 406 of the aerosol delivery device 400 by a user. Preferably, the elements of the aerosol generating component 430 do not experience thermal decomposition (e.g., charring, scorching, or burning) to any significant degree, and the aerosolized components are entrained in the air that is drawn through the aerosol delivery device 400, including a filter (if present), and into the mouth of the user.

In one implementation, the aerosol generating component may comprise a blend of flavorful and aromatic tobaccos in cut filler form. In another implementation, the aerosol generating component may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entireties. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the aerosol forming component may be formed from a wound roll of a reconstituted tobacco material. In another implementation, the substrate material may be formed from shreds, strips, and/or the like of a reconstituted tobacco material. In another implementation, the tobacco sheet may comprise a crimped sheet of reconstituted tobacco material. In some implementations, the substrate material may comprise overlapping layers (e.g., a gathered web), which may, or may not, include heat conducting constituents. Examples of aerosol forming components that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the aerosol generating components 430 may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, one or more of the substrate materials may include a plurality of microcapsules each formed into a hollow cylindrical shape. In some implementations, one or more of the substrate materials may include a binder material configured to maintain the structural shape and/or integrity of the plurality of microcapsules formed into the hollow cylindrical shape.

Tobacco materials useful in the present disclosure can vary and can include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT WO 02/37990 to Bereman; and Bombick et al., *Fund. Appl. Toxicol.,* 39, p. 11-17 (1997); which are incorporated herein by reference. Further example tobacco compositions that can be useful in a smoking device, including according to the present disclosure, are disclosed in U.S. Pat. No. 7,726,320 to Robinson et al., which is incorporated herein by reference in its entirety.

Still further, the aerosol generating component may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol generating component may comprise a blend of flavorful and aromatic tobaccos in cut filler form. In another aspect, the aerosol generating component may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entireties.

In some implementations, the aerosol generating component may include tobacco, a tobacco component, tobacco-derived material, and/or a non-tobacco material, that has been treated, manufactured, produced, and/or processed to incorporate an aerosol precursor composition (e.g., humectants such as, for example, propylene glycol, glycerin, and/or the like) and/or at least one flavoring agent, as well as a burn retardant (e.g., diammonium phosphate and/or another salt) configured to help prevent ignition, pyrolysis, combustion, and/or scorching of the aerosol delivery component by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

In some implementations, other flame/burn retardant materials and additives may be included within the aerosol generating component and my include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the aerosol generating component and/or other components (whether alone or in combination with each other and/or other materials), the desirable properties are preferably provided without undesirable off-gassing, chemically reactive, or melting-type behavior. Additional flavorants, flavoring agents, additives, and other possible enhancing constituents are described in U.S. patent application Ser. No. 15/707,461 to Phillips et al., which is incorporated herein by reference in its entirety.

In addition to the inhalable substance (e.g., flavors, nicotine, or pharmaceuticals generally), the aerosol generating component may comprise one or more aerosol-forming or vapor-forming materials, such as a polyhydric alcohol (e.g., glycerin, propylene glycol, or a mixture thereof) and/or water. Representative types of aerosol forming materials are set forth in U.S. Pat. No. 4,793,365 to Sensabaugh, Jr. et al.; and U.S. Pat. No. 5,101,839 to Jakob et al.; PCT WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference. A preferred aerosol forming material produces a visible aerosol upon the application of sufficient heat thereto, and a highly preferred aerosol forming material produces an aerosol that can be considered to be "smoke-like." Further tobacco materials, such as a tobacco aroma oil, a tobacco essence, a spray dried tobacco extract, a freeze dried tobacco extract, tobacco dust, or the like may be combined with the vapor-forming or aerosol-forming material. It is also understood that the inhalable substance itself may be in a form whereby, upon heating, the inhalable substance is released as a vapor, aerosol, or combination thereof. In other implementations, the inhalable substance may not necessarily release in a vapor or aerosol form, but the vapor-forming or aerosol-forming material that may be combined therewith can form a vapor or aerosol upon heating and function essentially as a carrier for the inhalable substance itself. Thus, the inhalable substance may be characterized as being coated on a substrate, as being absorbed in a substrate, as being adsorbed onto a surface of a substrate, or as being a natural component of the substrate (i.e., the material forming the substrate, such as a tobacco or a tobacco-derived material). Likewise, an aerosol-forming or vapor-forming material may be similarly characterized. In certain implementations, the aerosol generating component may particularly comprise a substrate with the inhalable substance and a separate aerosol forming material included therewith. As such, in use, the substrate may be heated, the aerosol forming material may be volatilized into a vapor form taking with it the inhalable substance. In a specific example, the aerosol generating component may comprise a solid substrate with a slurry of tobacco and an aerosol-forming material and/or vapor-forming material coated thereon or absorbed or adsorbed therein. The substrate component may be any material that does not combust or otherwise degrade at the temperatures described herein that the heating member achieves to facilitate release of the inhalable substance. For example, a paper material may be used, including a tobacco paper (e.g., a paper-like material comprising tobacco fibers and/or reconstituted tobacco). Thus, in various implementations, the aerosol generating component may be characterized as comprising the inhalable substance, alternately as comprising the inhalable substance and a separate aerosol-former or vapor-former, alternately as comprising the inhalable substance and a substrate, or alternately as comprising the aerosol generating component, the separate aerosol-former or vapor-former, and the substrate. Thus, the substrate may contain one or both of the inhalable substance and the aerosol-former or vapor-former.

If desired, the tobacco material or the aerosol generating component may generally further include other components, such as sugars, glycerin, vanilla, cocoa, licorice, and other flavoring materials, such as menthol. Example plant-derived compositions that may be used are disclosed in U.S. Pat. App. Pub. No. 2012/0152265 to Dube et al., and U.S. Pat. No. 9,107,453 to Dube et al. The selection of such further components may vary based upon factors such as the sensory characteristics that are desired for the present article, and the present disclosure is intended to encompass any such further components that may be readily apparent to those skilled in the art of tobacco and tobacco-related or tobacco-derived products. See, Gutcho, *Tobacco Flavoring Substances and Methods*, Noyes Data Corp. (1972) and Leffingwell et al., *Tobacco Flavoring for Smoking Products* (1972).

The inhalable substance and/or the separate vapor forming material may be provided on the aerosol generating component in a variety of configurations. For example, both materials may be associated with the aerosol generating component such that the concentration of each material along the length of the aerosol generating component is substantially constant (e.g., when dividing the substrate into a plurality of lengthwise segments, the total concentration of material in each individual segment can be substantially similar, such as varying by less than 10%, less than 5%, or less than 2% by mass). In other implementations, one or both of the materials may be present in a defined pattern. For example, the pattern may be a gradient wherein the concentration continually increases or decreases along the length of the substrate. In this manner, the first puff on the article may provide an amount of the inhalable substance that is significantly greater than or less than the amount of the inhalable substance in the last puff. The gradient may also be designed to provide uniform production of inhalable substance across all puffs. Moreover, the pattern may be such that a bolus of inhalable substance is provided at some point along the length of the substrate (e.g., corresponding to the first puff, the last puff, or some intermediate puff on the article). Any variety of such patterns may be envisioned in light of the present disclosure, and such variations are likewise encompassed by the present disclosure. Such patterning likewise may apply to further components as described herein (e.g., flavorants). For example, a bolus of a flavorant may be provided on the substrate in a position to substantially correspond to the last puff or the last two or three puffs on the article. The release of such flavor may signal to the consumer that the final puff on the device is approaching or has been achieved. Various other configurations and components that may be included in the aerosol generating component of the present disclosure are described in in U.S. Pat. No. 9,078,473 to Worm et al., which is incorporated herein by reference in its entirety.

In some aspects of the present disclosure, the aerosol generating component may be configured as an extruded material, as described in U.S. Pat. App. Pub. No. 2012/0042885 to Stone et al., which is incorporated herein by reference in its entirety. In still other aspects, the aerosol generating component may be configured as an extruded structure and/or substrate that includes, or is essentially comprised of tobacco, tobacco-related material, glycerin, water, and/or a binder material, although certain formulations exclude the binder material. In various implementations, the binder material may be any binder material commonly used for tobacco formulations including, for example, carboxymethyl cellulose (CMC), gum (e.g. guar gum), xanthan, pullulan, and/or an alginate. According to some aspects, the binder material included in the aerosol delivery component may be configured to substantially maintain a structural shape and/or integrity of the aerosol delivery component. Various representative binders, binder properties, usages of binders, and amounts of binders are set forth in U.S. Pat. No. 4,924,887 to Raker et al., which is incorporated herein by reference in its entirety.

In some implementations, the aerosol generating component may be further configured to substantially maintain its structure throughout the aerosol-generating process. That is, the aerosol generating component is configured to substantially maintain its shape (i.e., the aerosol delivery component does not continually deform under an applied shear stress) throughout the aerosol-generating process. Although in some implementations the aerosol generating component may include liquids and/or some moisture content, in some implementations the aerosol generating component is configured to remain substantially solid throughout the aerosol-generating process and substantially maintain its structural integrity throughout the aerosol-generating process. Example tobacco and/or tobacco related materials suitable for a substantially solid aerosol delivery component are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are all incorporated herein in their entireties by reference respectively.

In yet another aspect, the aerosol generating component may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents.

In various implementations, the aerosol generating component wall may be formed substantially of a material that can include the inhalable substance naturally therein (e.g., tobacco paper) or may be formed of any further material (e.g., paper) that can have the inhalable substance and/or the vapor-former or aerosol-former entrained therein. In addition to the inhalable substance and/or the vapor-forming or aerosol-forming substance, the substrate wall may comprise additional components. For example, a vapor barrier may be included on the outer surface of the aerosol generating component wall. Preferably, the vapor barrier is positioned on the wall surface that is adjacent (or in contact with) the heating member when the aerosol generating component is heated. In particular implementations, the vapor barrier may be formed of a material that is electrical insulating or may comprise a layer of electrically insulating material that can be in contact with the heating member. For example, a metal foil may be used as the vapor barrier, and the foil may have an insulating monolayer—e.g., a metal oxide layer—in contact with the heating member to prevent release of vapor or aerosol into the exterior volume of the aerosol generating component and facilitate release of the vapor or aerosol into an annular space defined by the inner surface of the aerosol generating component wall. Any vapor barrier material, such as a metal foil, may be used.

In further implementations, the aerosol generating component may be formed of a material that softens or changes phase (especially from solid to molten) at about the working temperature of the article. For example, the aerosol generating component may be a wax or a gel, and the inhalable substance may be entrained therein. In such implementations, it can be particularly useful to include the vapor barrier (or similar material) that provides support to the aerosol generating component and substantially prevents the aerosol generating component from contacting the heating member. Likewise, the aerosol generating component may comprise a vapor barrier layer coated with an inhalable substance and/or an aerosol forming material. For example, one or more of such coating materials may be in a microencapsulated form that preferably releases its components at a temperature within one or more of the working ranges otherwise described herein. Microencapsulation technology that may be useful in such implementations is disclosed, for example, in U.S. Pat. No. 4,464,434 to Davis.

In one implementation, the aerosol generating component may comprise a tobacco component (such as, for example, a reconstituted cast tobacco sheet or tobacco beads) or a non-tobacco component (such as, for example, herbs, paper, cellulose, etc.) with one or more of the following: a binder component, a humectant component, a flavor component, a moisturizer component, and a casing material. In some implementations, the binder component may include, for example, cellulose and/or guar gum. In some implementations, the humectant component may comprise glycerol, for example at approximately 15-25%, sorbitol at approximately 14.5%, and/or propylene glycol at approximately 3-10%. In some implementations, the flavor component may comprise, for example, acetic acid, citric acid, acetoin, lactic acid, menthol, peppermint oil, carob bin/extract, cocoa products, licorice extract, invent sugar, and/or sucrose. In some implementations, the moisturizer component comprise, for example, water at approximately 15-25%.

In the depicted implementation, the aerosol generating component 430, or a portion thereof, is wrapped in an overwrap material 432. In the depicted implementation, the overwrap material comprises an aluminum laminate; however, in other implementations the overwrap material may differ. In some implementations, the overwrap material may be formed of a heat conductive material and/or any material useful for providing additional structure and/or support for the aerosol source member. In various implementations, the overwrap material may comprise a material that resists (or promotes) transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material can incorporate inorganic components. In various implementations, the overwrap may be formed of multiple layers, such as an underlying, bulk layer, and an overlying layer, such as a typical wrapping paper in a cigarette. Such materials may include, for example, lightweight "rag fibers" such as flax, hemp, sisal, rice straw, and/or esparto. Further discussions relating to the configurations for overwrap materials that may be used with the present disclosure may be found in U.S. Pat. No. 9,078,473 to Worm et al., which is incorporated herein by reference in its entirety. In additional implementations, the overwrap material may have or more of the following qualities: it may be impermeable to the transfer of aerosol, it may have the ability to withstand the elevated temperature under consideration, it may promote the transfer of heat in the radial direction from the heater to the tobacco stick material, it may resist the transfer of heat in the axial direction along the tobacco stick away from the segment being heated, and/or it may have relatively low thermal mass so that it does not inhibit rapid temperature rises of the segment being heated. In one implementation, the overwrap material may be a stainless steel foil that, in some implementations, may be approximately 0.001" thick.

As noted, in the depicted implementation the aerosol source member 408 includes a filter 434. In various implementations, the filter may be made of various materials, including, for example, a cellulose acetate material, a polylactic resin material, and/or a polypropylene material. In various implementations, the filter may increase the structural integrity to the aerosol source member, and/or provide filtering capacity, if desired, and/or provide resistance to draw. For example, an article according to the disclosure can exhibit a pressure drop of about 50 to about 250 mm water pressure drop at 17.5 cc/second air flow. In further implementations, pressure drop can be about 60 mm to about 180 mm or about 70 mm to about 150 mm Pressure drop value may be measured using a Filtrona Filter Test Station (CTS Series) available from Filtrona Instruments and Automation Ltd or a Quality Test Module (QTM) available from the Cerulean Division of Molins, PLC. The length of the filter at the mouth end of the aerosol source member can vary—e.g., about 2 mm to about 20 mm, about 5 mm to about 20 mm, or about 10 mm to about 15 mm. In some implementations, the filter may be separate from the overwrap, and in other implementations the filter may be held in position by the overwrap.

Additional example types of overwrapping materials, wrapping material components, and treated wrapping materials that may be used in overwrap in the present disclosure are described in U.S. Pat. No. 5,105,838 to White et al.; U.S. Pat. No. 5,271,419 to Arzonico et al.; U.S. Pat. No. 5,220,930 to Gentry; U.S. Pat. No. 6,908,874 to Woodhead et al.; U.S. Pat. No. 6,929,013 to Ashcraft et al.; U.S. Pat. No. 7,195,019 to Hancock et al.; U.S. Pat. No. 7,276,120 to Holmes; U.S. Pat. No. 7,275,548 to Hancock et al.; PCT WO 01/08514 to Fournier et al.; and PCT WO 03/043450 to Hajaligol et al., which are incorporated herein by reference in their entireties. Representative wrapping materials are commercially available as R. J. Reynolds Tobacco Company Grades 119, 170, 419, 453, 454, 456, 465, 466, 490, 525, 535, 557, 652, 664, 672, 676 and 680 from Schweitzer-Maudit International. The porosity of the wrapping material can vary, and frequently is between about 5 CORESTA units and about 30,000 CORESTA units, often is between about 10 CORESTA units and about 90 CORESTA units, and frequently is between about 8 CORESTA units and about 80 CORESTA units.

To maximize aerosol and flavor delivery which otherwise may be diluted by radial (i.e., outside) air infiltration through the overwrap, one or more layers of non-porous cigarette paper may be used to envelop the aerosol source member (with or without the overwrap present). Examples of suitable non-porous cigarette papers are commercially available from Kimberly-Clark Corp. as KC-63-5, P878-5, P878-16-2 and 780-63-5. Preferably, the overwrap is a material that is substantially impermeable to the vapor formed during use of the inventive article. If desired, the overwrap can comprise a resilient paperboard material, foil-lined paperboard, metal, polymeric materials, or the like, and this material can be circumscribed by a cigarette paper wrap. The overwrap may comprise a tipping paper that circumscribes the component and optionally may be used to attach a filter material to the aerosol source member, as otherwise described herein. In various implementations, other components may exist between the aerosol generating component and the mouth end of the aerosol source member, wherein the mouth end may include a filter. For example, in some implementations one or any combination of the following may be positioned between the aerosol generating component and the mouth end: an air gap; phase change materials for cooling air; flavor releasing media; ion exchange fibers capable of selective chemical adsorption; aerogel particles as filter medium; and other suitable materials.

When the overwrap material is present, the overall length thereof can vary from being substantially identical to the length of the aerosol generating component up to about two times the length of the aerosol generating component. Thus, the aerosol generating component may have a length that is up to about 50%, up to about 30%, or up to about 10% less than the length of the overwrap. Preferably, the aerosol generating component may have a length that is at least 10%, at least 15%, or at least 20% less than the length of the overwrap. More specifically, the distance the overwrap extends beyond the aerosol generating component may be about 5%, about 10%, about 15%, about 20%, about 25%, about 30%, about 40%, about 50%, about 60%, about 70%, about 80%, about 90%, or about 100% of the length of the aerosol generating component.

Figure 11:
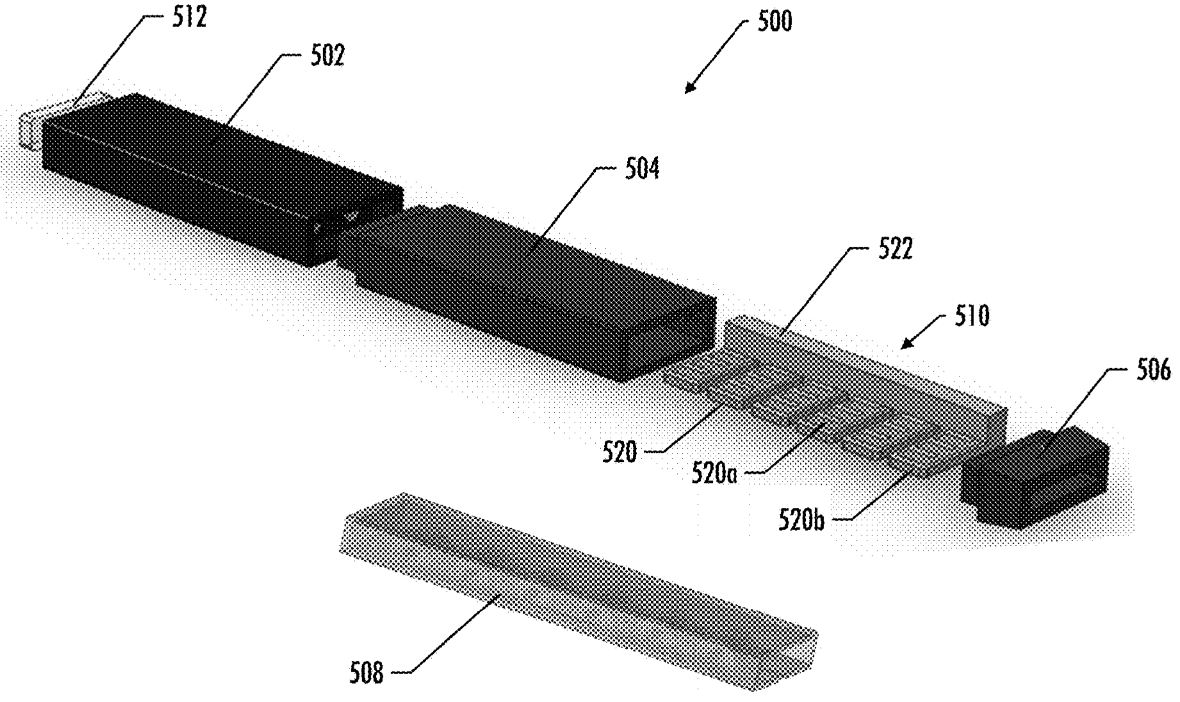
FIG. 11 illustrates a perspective exploded view of an aerosol source member, in accordance with an example implementation of the present disclosure.

FIG. 11 illustrates a perspective exploded view of an aerosol source member 500, in accordance with an example implementation of the present disclosure. In particular, the aerosol delivery device 500 of the depicted implementation includes a first housing portion 502, a second housing portion 504, a mouthpiece 506, an aerosol source member 508 (in the form of a cartridge that includes a liquid or semi-liquid aerosol generating component), a heating assembly 510, and an indicator 512. The aerosol delivery device 500 further includes an electrical energy source (not visible, e.g., a battery, which may be rechargeable, and/or a rechargeable supercapacitor), and a control component, (not visible, e.g., a microprocessor, individually or as part of a microcontroller, a printed circuit board (PCB) that includes a microprocessor and/or microcontroller, etc.). As will be discussed in more detail below, the heating assembly 510 of various implementations comprises a series of independent and distinct heating members, wherein each heating member is configured to heat a segment of the aerosol source member 508.

In various implementations, one or both of the control component and the electrical energy source may be coupled with the first housing portion 502. For the sake of the current application, the phrase "coupled with" when used with respect to one component relative to another may encompass implementations in which one component is located within another component and/or implementations wherein one component is separate but otherwise operatively connected to another component. For example, in the depicted implementation, both the control component and the electrical energy source are located within the first housing portion 502; however, in other implementations one or both of the control component and the electrical energy source may be located in different components. Further information regarding the control component and the electrical energy source is provided below.

In various implementations, the first housing portion 502 and the second housing portion 504 may be mechanically engaged together in a variety of ways. For example, in some implementations, the first housing portion 502 and the second housing portion 504 may engage via a threaded connection. In other implementations, the first housing portion 502 and the second housing portion 504 may engage via an interference or friction fit. In other implementations, the first housing portion 502 and the second housing portion 504 may engage via a magnetic connection. In other implementations, the first housing portion 502 and the second housing portion 504, may engage via a snap fit connection. In still other implementations, the first housing portion 502 and the second housing portion 504 engage via a bayonet-type connection that includes a male component (e.g., a pin) and a female component (e.g., an L-shaped slot). It should be noted that in some implementations, the first housing portion 502 and the second housing portion 504 may comprise a single, unitary housing portion.

Although other implementations may differ, in the depicted implementation the aerosol source member 508 is inserted into the second housing portion 504 by removing the mouthpiece 506 and inserting the aerosol source member 508 so that it is positioned proximate the heating assembly 510. In various implementations, one or both the second housing portion 504 or the aerosol source member 508 may be keyed or may include one or more stopping or locating features to aid in the proper placement of the aerosol source member 508. In the depicted implementation, there is a single series of heating elements 520 that extend from the heating assembly frame 522 such that they are configured to be positioned on one side of the aerosol source member 508; however, in other implementations there may be two or more series of heating elements 520 that are configured to be positioned on opposite sides of the aerosol source member 508. After insertion of the aerosol source member 508, the mouthpiece can then be reinserted into the second housing portion 504. In various implementations, the mouthpiece may attach to the second attachment portion in a variety of different ways, including, for example, via a press fit attachment, a threaded attachment, a hinge attachment, a magnetic attachment, etc. In various implementations, the first housing portion 502, the second housing 504, and/or the mouthpiece 506 may be detachable from each other, and thus any one or all may be replaceable.

In some implementations, the first housing portion 502 and/or the second housing portion 504 may also include one or more pushbuttons configured to activate certain operations of the device 500, such as, for example, turning on the device and initiating heating of the heating assembly 510 (e.g., one or more heating elements of the heating assembly). As will be discussed in more detail below, in various implementations, the aerosol source member 508 may comprise an aerosol generating component, which is configured to be located proximate the heating assembly 510. It should be noted that while the first housing portion 502, the second housing portion 504, and the aerosol source member 508 of the depicted implementation have a substantially elongate rectangular cuboid shape, in other implementations the first housing portion 502, the second housing portion 504, and/or the aerosol source member 508 may have any other shape, including, for example, the shape of a conventional cigarette or cigar.

In specific implementations, the first housing portion 502, the second housing portion 504, and/or the aerosol source member 508 may be referred to as being disposable or as being reusable. For example, the electrical energy source and/or the first housing portion 502 containing the electrical energy source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 508 and/or the second housing portion 504 containing the aerosol source member 508, and/or the mouthpiece 506 may comprise a single-use device. A single use component for use with a control body is disclosed in U.S. Pat. No. 8,910,639 to Chang et al., which is incorporated herein by reference in its entirety.

In various implementations, the control component may comprise a control circuit (which may be connected to further components, as further described herein) that may be connected by electrically conductive wires to the electrical energy source. In various implementations, the control component may control when and how the heating assembly 510 (e.g., one or more heating members) receives electrical energy to heat the aerosol generating component for release of the inhalable substance for inhalation by a consumer. Such control can relate to actuation of pressure sensitive switches or the like, which are described in greater detail hereinafter. It should be noted that the terms "connected" or "coupled" should not be read as necessitating direct connection without an intervening component. Rather, these terms may encompass direct connection and/or connection via one or more intervening components. As such, in various implementations these terms may be understood to mean operatively connected to or operatively coupled with. In various implementations, the control component of the present disclosure may comprise the control component described in U.S. patent application Ser. No. 15/976,526, filed on May 10, 2018, and titled Control Component for Segmented Heating in an Aerosol Delivery Device, which is incorporated herein by reference in its entirety.

In various implementations, the control component may also be configured to closely control the amount of heat provided to the aerosol generating component of the aerosol source member. While the heat needed to volatilize the aerosol generating component in a sufficient volume to provide a desired dosing of the inhalable substance for a single puff can vary for each particular substance used, it can be particularly useful for the heating member to heat to a temperature of at least 120° C., at least 130° C., or at least 140° C. In some implementations, in order to volatilize an appropriate amount of the aerosol generating component and thus provide a desired dosing of the inhalable substance, the heating temperature may be at least 150° C., at least 200° C., at least 300° C., or at least 350° C. It can be particularly desirable, however, to avoid heating to temperatures substantially in excess of about 550° C. in order to avoid degradation and/or excessive, premature volatilization of the aerosol generating component. The present disclosure may particularly provide the components of the present article in combinations and modes of use that will yield the inhalable substance in desired amounts at relatively low temperatures. As such, yielding can refer to one or both of generation of the aerosol within the article and delivery out of the article to a consumer. In specific implementations, the heating temperature may be about 120° C. to about 300° C., about 130° C. to about 290° C., about 140° C. to about 280° C., about 150° C. to about 250° C., or about 160° C. to about 200° C. The duration of heating can be controlled by a number of factors, as discussed in greater detail hereinbelow. Heating temperature and duration may depend upon the desired volume of aerosol and ambient air that is desired to be drawn through the aerosol source member, as further described herein. The duration, however, may be varied depending upon the heating rate of the heating members, as the article may be configured such that the heating members are energized only until a desired temperature is reached. Alternatively, duration of heating may be coupled to the duration of a puff on the article by a consumer. Generally, the temperature and time of heating will be controlled by one or more components contained in the control body, as noted above.

The amount of inhalable material released by the aerosol source member can vary based upon the nature of the aerosol forming component. Preferably, the aerosol source member is configured with a sufficient amount of the aerosol forming component, with a sufficient amount of any aerosol-former, and to function at a sufficient temperature for a sufficient time to release a desired amount over a course of use. The amount may be provided in a single inhalation from the aerosol source member or may be divided so as to be provided through a number of puffs from the article over a relatively short length of time (e.g., less than 30 minutes, less than 20 minutes, less than 15 minutes, less than 10 minutes, or less than 5 minutes). For example, the device may provide nicotine in an amount of about 0.01 mg to about 0.10 mg, about 0.05 mg to about 1.0 mg, about 0.08 mg to about 0.5 mg, about 0.1 mg to about 0.3 mg, or about 0.15 mg to about 0.25 mg per puff on the aerosol source member. In other implementations, a desired amount may be characterized in relation to the amount of wet total particulate matter delivered based on puff duration and volume. For example, the aerosol source member may deliver at least 1.0 mg of wet total particulate matter on each puff, for a defined number of puffs (as otherwise described herein), when smoked under standard FTC smoking conditions of 2 second, 35 ml puffs. Such testing may be carried out using any standard smoking machine. In other implementations, the amount of total particulate matter (TPM) yielded under the same conditions on each puff may be at least 1.5 mg, at least 1.7 mg, at least 2.0 mg, at least 2.5 mg, at least 3.0 mg, about 1.0 mg to about 5.0 mg, about 1.5 mg to about 4.0 mg, about 2.0 mg to about 4.0 mg, about 2.0 mg to about 3.0 mg, about 4.0 mg to about 6.0 mg, about 6.0 mg to about 8.0 mg, or about 8.0 mg to about 10.0 mg.

As noted, the aerosol delivery device 500 of some implementations may include a pushbutton, which may be linked to the control component for manual control of the heating members. For example, in some implementations the consumer may use the pushbutton to energize the heating assembly 510. Similar functionality tied to the pushbutton may be achieved by other mechanical means or non-mechanical means (e.g., magnetic or electromagnetic). Thusly, activation of the heating assembly 510 may be controlled by a single pushbutton. Alternatively, multiple pushbuttons may be provided to control various actions separately. In some implementations, one or more pushbuttons present may be substantially flush with the casing of the first housing portion 502 and/or the second housing portion 504.

Instead of (or in addition to) any pushbuttons, the aerosol delivery device 500 of the present disclosure may include components that energize the heating assembly 510 in response to the consumer's drawing on the article (i.e., puff-actuated heating). For example, the device may include a switch or flow sensor (not shown) in the first housing portion 502, and/or the second housing portion 504, and/or the mouthpiece 506 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch, or a touch sensor (e.g., capacitive touch sensor) configured to sense contact between a user (e.g., mouth or fingers of user) and one or more surfaces of the aerosol delivery device 500. An example mechanism that can provide such puff-actuation capability includes a Model 163PC01D36 silicon sensor, manufactured by the MicroSwitch division of Honeywell, Inc., Freeport, Ill. With such sensor, the heating assembly 510 may be activated rapidly by a change in pressure when the consumer draws on the device. In addition, flow sensing devices, such as those using hot-wire anemometry principles, may be used to cause the energizing of the heating assembly sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and aerosol source member may be included in the first housing portion 502 and/or the second housing portion 504 so that pressure changes during draw are readily identified by the switch. Other example puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In some implementations, when the consumer draws on the mouthpiece 506, the current actuation means may permit unrestricted or uninterrupted flow of current through the heating assembly 510 to generate heat rapidly. Because of the rapid heating, it can be useful to include current regulating components to (i) regulate current flow through the heating members to control heating of the resistance element and the temperature experienced thereby, and (ii) prevent overheating and degradation of the aerosol generating component. In some implementations, the current regulating circuit may be time-based. Specifically, such a circuit may include a means for permitting uninterrupted current flow through the heating members for an initial time period during draw, and a timer means for subsequently regulating current flow until draw is completed. For example, the subsequent regulation can include the rapid on-off switching of current flow (e.g., on the order of about every 1 to 50 milliseconds) to maintain the heating members within the desired temperature range. Further, regulation may comprise simply allowing uninterrupted current flow until the desired temperature is achieved then turning off the current flow completely. The heating members may be reactivated by the consumer initiating another puff on the article (or manually actuating the pushbutton, depending upon the specific switch implementation employed for activating the heater). Alternatively, the subsequent regulation can involve the modulation of current flow through the heating members to maintain the heating members within a desired temperature range. In some implementations, so as to release the desired dosing of the inhalable substance, the heating members may be energized for a duration of about 0.2 second to about 5.0 seconds, about 0.3 second to about 4.0 seconds, about 0.4 second to about 3.0 seconds, about 0.5 second to about 2.0 seconds, or about 0.6 second to about 1.5 seconds. One example time-based current regulating circuit can include a transistor, a timer, a comparator, and a capacitor. Suitable transistors, timers, comparators, and capacitors are commercially available and will be apparent to the skilled artisan. Example timers are those available from NEC Electronics as C-1555C and from General Electric Intersil, Inc. as ICM7555, as well as various other sizes and configurations of so-called "555 Timers". An example comparator is available from National Semiconductor as LM311. Further description of such time-based current regulating circuits is provided in U.S. Pat. No. 4,947,874 to Brooks et al., which is incorporated herein by reference in its entirety.

In light of the foregoing, it can be seen that a variety of mechanisms can be employed to facilitate actuation/deactuation of current to the heating members. For example, the device may include a timer for regulating current flow in the article (such as during draw by a consumer). The device may further include a timer responsive switch that enables and disables current flow to the heating members. Current flow regulation also can comprise use of a capacitor and components for charging and discharging the capacitor at a defined rate (e.g., a rate that approximates a rate at which the heating member heats and cools). Current flow specifically may be regulated such that there is uninterrupted current flow through the heating members for an initial time period during draw, but the current flow may be turned off or cycled alternately off and on after the initial time period until draw is completed. Such cycling may be controlled by a timer, as discussed above, which can generate a preset switching cycle. In specific implementations, the timer may generate a periodic digital wave form. The flow during the initial time period further may be regulated by use of a comparator that compares a first voltage at a first input to a threshold voltage at a threshold input and generates an output signal when the first voltage is equal to the threshold voltage, which enables the timer. Such implementations further can include components for generating the threshold voltage at the threshold input and components for generating the threshold voltage at the first input upon passage of the initial time period.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties. Another method uses an electrical resistance change for actuating the aerosol delivery device and/or the heating assembly thereof. It works by using a very thin small metallic probe in the form of strip or wire that is installed perpendicular to the air flow inside the cartridge. The air flow generated by the user applies mechanical force on the probe and folds it to some extent. Due to this change in geometry that results in bending/tension in part of the probe, a change in electrical resistance of the probe occurs, this resistance alteration is sent as a pulse/information to the PCB and works as a trigger to activate the heating assembly 510.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. patent application Ser. No. 14/881,392 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

As noted above, the electrical energy source used to provide power to the various electrical components of the device 500 may take on various implementations. Preferably, the electrical energy source is able to deliver sufficient energy to rapidly heat the heating members in the manner described above and power the device through use with multiple aerosol source members 508 while still fitting conveniently in the device 500. Examples of useful electrical energy sources include lithium-ion batteries that are preferably rechargeable (e.g., a rechargeable lithium-manganese dioxide battery). In particular, lithium polymer batteries can be used as such batteries can provide increased safety. Other types of batteries—e.g., nickel-cadmium cells— may also be used. Additionally, a preferred electrical energy source is of a sufficiently light weight to not detract from a desirable smoking experience. Some examples of possible electrical energy sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

One example of an electrical energy source is a TKI-1550 rechargeable lithium-ion battery produced by Tadiran Batteries GmbH of Germany. In another implementation, a useful electrical energy source may be a N50-AAA CADNICA nickel-cadmium cell produced by Sanyo Electric Company, Ltd., of Japan. In other implementations, a plurality of such batteries, for example providing 1.2-volts each, may be connected in series. Other electrical energy sources, such as rechargeable lithium-manganese dioxide batteries, may also be used. Any of these batteries or combinations thereof may be used in the electrical energy source, but rechargeable batteries are preferred because of cost and disposal considerations associated with disposable batteries. In implementations where rechargeable batteries are used, the aerosol delivery device 500 may further include charging contacts for interaction with corresponding contacts in a conventional recharging unit (not shown) deriving power from a standard 120-volt AC wall outlet, or other sources such as an automobile electrical system or a separate portable power supply. In further implementations, the electrical energy source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the device 500. Thus, the present disclosure also may include a charger component that can be attached to the device between uses to replenish the supercapacitor. Thin film batteries may be used in certain implementations of the present disclosure.

As noted above, in various implementations, the aerosol delivery device 500 may comprise one or more indicators, such as indicator 512, which in the depicted implementation is located proximate a distal end of the first housing portion 502. In various implementations, the one or more indicators may be located at any location on the first housing portion 502, and/or the second housing portion 504, and/or the mouthpiece 506. In some implementations, an indicator may comprise a light (e.g., a single or multi-color light emitting diode (LED)) that may provide indication of multiple aspects of use of the device. For example, in some implementations a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In still other implementations, only a single indicator may be present, and lighting thereof may indicate that current was flowing to the heating member and the device is actively heating. This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In various implementations, the first housing portion 502, and/or the second housing portion 504, and/or the mouthpiece 506 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as further discussed herein. In some implementations, a heat resistant polymer may be used. In other implementations, ceramic materials may be used. In further implementations, an insulating material may be used so as not to unnecessarily move heat away from the aerosol source member. The housing, when formed of a single layer, may have a thickness that preferably is about 0.2 mm to about 5.0 mm, about 0.5 mm to about 4.0 mm, about 0.5 mm to about 3.0 mm, or about 1.0 mm to about 3.0 mm. Further example types of components and materials that may be used to provide the functions described above or be used as alternatives to the materials and components noted above can be those of the types set forth in U.S. Pat. App. Pub. Nos. 2010/00186757 to Crooks et al.; 2010/00186757 to Crooks et al.; and 2011/0041861 to Sebastian et al.; the disclosures of the documents being incorporated herein by reference in their entireties.

As shown in FIG. 11, the depicted implementation includes a heating assembly 510 that includes a series of individual resistive heating elements 520 that extend from a heating assembly frame 522. In the depicted implementation, there are six individual heating elements 520; however, in other implementations there may be any number of heating elements, including, for example, as few as one, or more than six, such as, for example, sixteen heating elements. In various implementations, the control component is configured to control the individual heating elements 520 independently and/or in any combination, with activation of the heating elements 520 being initiated using any of the methods described above. In the depicted implementation, each of the heating elements 520 is configured to heat a segment of the aerosol source member 508. The heating elements 520 of the depicted implementation comprise resistive heating elements and have a substantially planar rectangular shape, although in other implementations the heating elements 520 may have other shapes. Resistive heating elements may be configured to produce heat when an electrical current is directed therethrough. Such heating elements often comprise a metal material and are configured to produce heat as a result of the electrical resistance associated with passing an electrical current therethrough. In the depicted implementation, each of the heating elements includes a heating element wire and/or trace 520*a* (hereinafter referred to as a "heating trace") that is constructed of an electrically resistant material. Examples of electrically resistive materials include, but are not limited to, titanium, silver, nickel, nichrome, stainless steel, various metal alloys, ceramics such as silicon carbide and silicon nitride, composites, and/or any combination thereof. In various implementations, each heating trace 520*a* may be fixed on a main body portion 520*b*, which in the depicted implementation may be an extension of, or part of, the heating assembly frame 522. In various implementations, each heating trace 520*a* may be created on a corresponding main body portion 520*b* via printing, embedding, machining, squeeze casting, etc. In various implementations, the heating assembly frame 522 and/or the main body portion 520*b* may be constructed of a metal material (e.g., aluminum, stainless steel, metal alloys, etc.); however, in other implementations, the heating assembly frame 522 and/or the main body 520*b* may be constructed of another material, including, for example, a ceramic material (e.g., alumina, silica, mullite, silicon carbide, silicon nitride, aluminum nitride, etc.), a polymer material (e.g., polyimide, thermoplastic polyimide, polybenzimidazole, polyether ether ketone, polypropylene, high density polyethylene, etc.) composite materials, and/or any combinations thereof.

Figure 12:
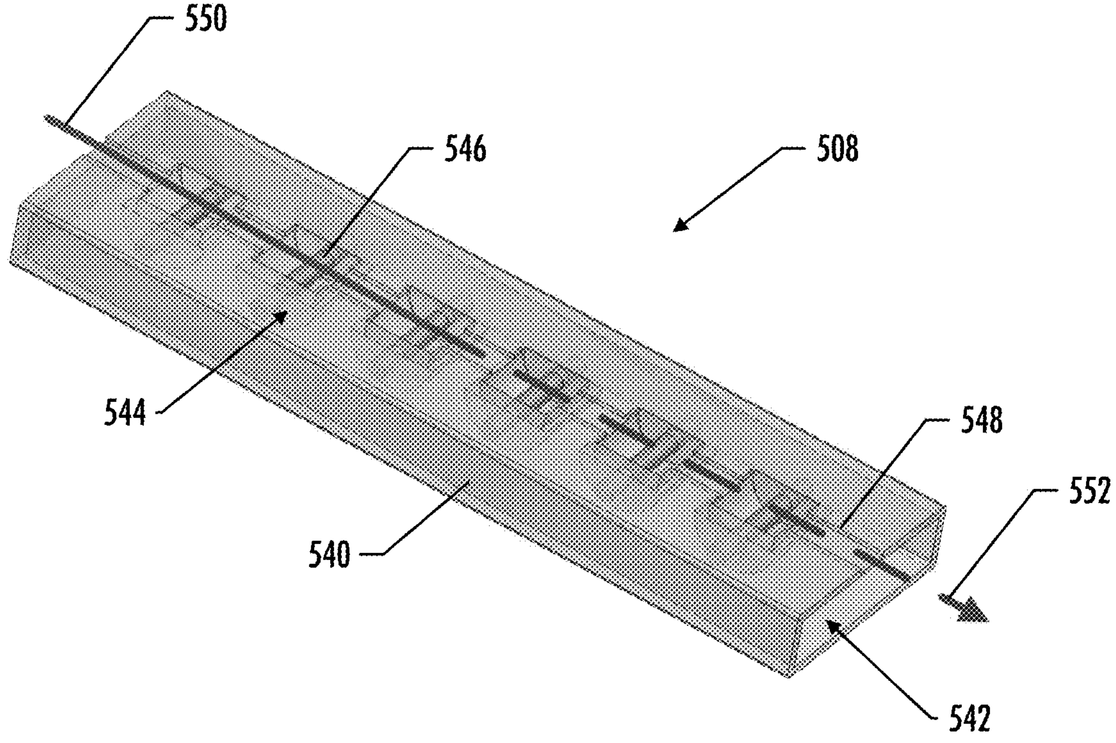
FIG. 12 illustrates a perspective view of a cartridge of an aerosol source member, in accordance with an example implementation of the present disclosure.

FIG. 12 illustrates a perspective view of an aerosol source member 508 in the form of a reservoir cartridge, in accordance with an example implementation of the present disclosure. In various implementations the aerosol source member 508 includes a reservoir housing 540, a reservoir 542, and a series of atomizer chambers 544, each of which includes a liquid transport element 546. As will be discussed in more detail below, the series of atomizer chambers 544 are configured to substantially align with the series of heating elements 520 of the heating assembly 510. In various implementations, the reservoir housing 540 may be constructed of one or more of a variety of materials, including, for example, a metal material, a ceramic material, a glass material, and/or a plastic material, such as, for example, an acrylic material (e.g., polymethlamethacrylate). In some implementations, the reservoir housing 540 may comprise a translucent or transparent material, such that a user may view the quantity of the aerosol generating component remaining therein. In the depicted implementation, the reservoir housing 540 is constructed of polypropelene or Tritan™, although in other implementations, other materials are possible In various implementations, the reservoir 542 may hold an aerosol generating component, which may be in the form of a liquid or semi-liquid aerosol precursor composition. Some representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor composition, and are described, by way of example, in U.S. Pat. App. Pub. No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein in their entireties. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties.

The reservoir housing 540 may include an aerosol channel 548 that extends from one end of the reservoir housing 540, to the other end of the reservoir housing 540. In particular, in some implementations the aerosol channel 548 extends from a distal end of the reservoir housing 540 to an end of the aerosol housing 540 that is proximate the mouthpiece 506 when the aerosol source member 508 is inserted into the second housing portion 504. In various implementations, the aerosol channel 548 may comprise a groove or slot in the reservoir housing 540 that crosses over each of the atomizer chambers 544. In such a manner, when a user draws on the aerosol delivery device 500, the drawn air passes over the atomizer channels 544 and may pick up any aerosol that is generated in one or more of the atomizer chambers 544.

In the depicted implementation, the aerosol source member 508 includes six atomizer chambers 544 (and thus six liquid transport elements 546). In various implementations, the liquid transport elements 546 may comprise porous monoliths. For example, in the depicted implementation, the liquid transport elements 546 may comprise a ceramic material such that aerosol precursor composition delivered to the liquid transport elements 546 may be absorbed therein for aerosolization. In other implementations, the liquid transport elements may comprise other materials, including, for example cotton, silica, cellulose, and other fibrous materials. Although in various implementations the size and shape of the atomizer chambers may vary, in the depicted implementation the atomizer chambers 544 have a substantially half-cylinder shape, wherein each respective liquid transport element 546 extends from one end of the atomizer chamber 544 to the other end in an orientation substantially perpendicular and slightly below the aerosol channel 548. In particular, the ends of each liquid transport element 546 extend through the reservoir housing 540 such that the liquid transport elements 546 are in fluid contact with the aerosol precursor composition contained in the reservoir 542 such that the aerosol precursor composition flows (e.g., via capillary action) into the liquid transport elements 546.

An electrical connection between the control component and the heating assembly 510 allows the control component to direct electrical current to the heating assembly 510, such as upon actuation by the user (e.g., via a button) and/or when a puff on the aerosol delivery device is detected. A noted above, the aerosol delivery device 500 of the depicted implementation includes a mouthpiece 506. When a user draws on the mouthpiece 506, air 550 may be directed through one or more air intakes in the device 500 from the environment and into the distal end of the aerosol channel 548. In some implementations, the air 550 may enter the device 500 through one or more openings in the first housing portion 502 and/or the second housing portion 504. In some implementations, the air 550 may additionally or alternatively enter through an opening between the first housing portion 502 and the second housing portion 504. Other possible entry openings are described in U.S. Pat. No. 9,220,302 to DePiano et al., which is incorporated herein by reference in its entirety.

In some implementations, a sensor in the aerosol delivery device 500 (e.g., the flow sensor) may sense the puff. When the puff is sensed, the control component may direct current to one or more of the heating elements 520. Accordingly, one or more of the heating elements 520 may vaporize the aerosol precursor composition contained in the one or more liquid transport elements 546 located proximate the activated heating elements 520. As the air 550 enters the atomizer chambers 544, it travels past (and/or around) the liquid transport element 546. At such point, if the respective heating element 520 is active, the air 550 mixes with the vaporized aerosol precursor composition and becomes the aerosol 552.

The air drawn into the aerosol channel 548 may be drawn past each of the atomizer chambers 544, such that the air 550 exits through the opposite end of the aerosol channel 548 and through the mouthpiece 506 of the device 500. As illustrated, for example, if only the third heating element 520 is activated, the drawn air 550 will be mixed with the aerosol formed in the third atomizer chamber 544. As such, for example, if multiple heating elements 520 are activated, the air 550 will pick up aerosol from the multiple atomizer chambers 544.

In some implementations, at least a portion of the reservoir 542 may comprise a plurality of layers of nonwoven fibers. Thus, liquid components, for example, can be sorptively retained in the reservoir 542. In various implementations, the reservoir 542 is in fluid connection with the series of atomizer chambers 544. Thus, each liquid transport element 546 may be configured to transport liquid from the reservoir 542 proximate a corresponding heating element 520 of the plurality of heating elements 520 via capillary action or other liquid transport mechanism.

In the depicted implementation, the reservoir 542 comprises a single reservoir compartment wherein all of the liquid transport elements 546 are in contact with the same liquid composition; however, in other implementations, there may be two or more separate reservoir compartments, each of which may encompass one or more of the atomizer chambers. For example, in some implementations, the reservoir 542 may include two or more separate reservoir compartments that are sealingly independent from each other. In such a manner, for example, some atomizer chambers may be separate from each other such that some of the liquid transport elements 546 are not in contact with the same liquid composition. For example, in some implementations where there are six atomizer chambers, there may be two, three, four, five, or six separate reservoir chambers, each of which may contain a different liquid composition. As an example, one or more of the separate reservoir compartments may include different aerosol precursor compositions and/or different flavorants such that a user may be able to choose between the one or more aerosol precursor compositions and/or flavorants as desired. In other implementations, separate sub-reservoirs containing different substances may be heated to contribute to or add to a vapor produced by the device. For example, one sub-reservoir may contain a nicotine-containing liquid and another sub-reservoir may contain a flavorant (which, for example, may be selectable from multiple sub-reservoirs containing flavorants), the nicotine-containing liquid and the flavorant being added to the vapor produced by the device. In another example, two sub-reservoirs may be simultaneously heated to create a binary reaction in the produced vapor. For example, a sub-reservoir containing an acidic liquid (such as, for example, a lactic acid) may be heated and combined with a sub-reservoir containing a nicotine-liquid to form a nicotine salt in the vapor. Because the number of possible separate heating elements and/or reservoir compartments may vary, in some implementations a user may select among a nearly infinite number of combinations of aerosol precursor compositions and/or aerosol precursor compositions flavorants.

As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Some possible components that may be included in an aerosol source member cartridge are provided, for example, in U.S. Pat. App. Pub. No. 2014/0261495 to DePiano et al., which is incorporated herein by reference in its entirety. Additional components that may be included in an aerosol source member cartridge and details relating thereto are provided, for example, in U.S. Pat. Pub. No. 2015/0335071 to Brinkley et al., filed May 23, 2014, which is incorporated herein by reference in its entirety. Various other components that may be applicable to an aerosol delivery device according to the present disclosure can be chosen from components described in the art and commercially available. Reference is made, for example, to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

With regard to any of the implementations described above, the overall function of a device may vary, based on the requirements of a particular application. In one implementation, for example, once an aerosol source member has been inserted into the device and with the heating assembly in a heating (e.g., closed) position, the device may be initially activated using a switch and/or pushbutton as described above. Preheating may be the next operation and may occur for approximately 20-30 seconds. Within the preheating period, a particular current/voltage passing through the heating assembly (e.g., the heating elements) may cause the temperature of the heating elements to reach approximately 100-120° C. A temperature sensor (e.g., a resistance temperature detector) may be included so as to control the preheating temperature so that it does not surpass the desired preheating temperature.

After preheating is finished, individual heating elements may be activated, which in some implementations may be triggered by a user by drawing air into the device. In some implementations, the heating element temperature may crest at 250-350° C. during each draw. Some implementations may include pressure sensors to measure the pressure changes in the device to activate one or more the heating elements with regard to each air drawing. The device may further be configured so that power can be switched/controlled between/among the elements through the control component using one or more stimuli. For example, in some implementations the stimuli may relate to the number of puffs and/or other parameters, such as, for example, temperature changes in the heating elements.

In some implementations, a heating element may be energized subsequent to a preheating period triggered by a first draw on the device. The heating element may be energized again for second and third draws on the device. The number of times that each heating element is energized can be adjusted depending on the total number of the heating elements, resistance, and size of the heating elements, and the electric power of the heating elements. After a segment of the aerosol generating component associated with a heating element has been consumed, another heating element, such as, for example, the next heating element, may be activated. In some implementations, the device may be configured so that power may be controlled to a subsequent heating element every time the user switches on the device. In some implementations, a heating cycle may be reset to zero and may start over after energizing the last heating element in the series and/or when the aerosol source member is removed or inserted into the device by a user. Additional functional characteristics that may be applicable to the present aerosol delivery device are described in U.S. patent application Ser. No. 15/976,526, filed on May 10, 2018, and titled Control Component for Segmented Heating in an Aerosol Delivery Device, which is incorporated herein by reference in its entirety.

It should be noted for any of the aerosol delivery device described above, the same device may be configured to accommodate either an aerosol source member having a solid or semi-solid aerosol generating component (e.g., similar to the aerosol source member 408) or an aerosol source member having a liquid or semi-liquid aerosol generating component (e.g., similar to the aerosol source member 508). In such a manner, the control component of that particular device may be configured to adjust or control various parameters (e.g., heating temperatures, heating times, etc.) to accommodate the particular aerosol generating component used with the device.

Although the various figures described herein illustrate the housing or housing portions and the aerosol source member in a working relationship, it is understood that the housing or housing portions and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a housing or one or more housing portions with one or more aerosol source members. A kit may further comprise a housing or one or more housing portions with one or more charging components. A kit may further comprise a housing or one or more housing portions with one or more batteries. A kit may further comprise a housing or one or more housing portions with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the housing or housing portions may be provided with a heating assembly inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:

a control body having an outer housing;

an electrical energy source located within the housing;

a control component operatively connected to the electrical energy source;

a heating assembly operatively connected to the control component; and an aerosol source member that includes an aerosol generating component configured to be positioned proximate the heating assembly, wherein the aerosol source member comprises a reservoir cartridge and the aerosol generating component comprises a liquid aerosol precursor composition, wherein the heating assembly comprises a series of heating elements, and wherein the reservoir cartridge defines a series of atomizer chambers, wherein the reservoir cartridge includes an aerosol channel, wherein the aerosol channel comprises a groove or slot, and wherein the aerosol channel crosses over and interconnects each of the atomizer chambers.

2. The aerosol delivery device of claim 1, wherein the series of atomizer chambers are configured to substantially align with the series of heating elements.

3. The aerosol delivery device of claim 1, wherein a separate liquid transport element extends through each atomizer chamber.

4. The aerosol delivery device of claim 3, wherein each of the heating elements is configured to be located proximate a corresponding atomizer chamber.

5. The aerosol delivery device of claim 3, wherein the liquid transport elements comprise a porous monolith.

6. The aerosol delivery device of claim 3, wherein the liquid transport elements comprise a fibrous material.

7. The aerosol delivery device of claim 3, wherein the liquid transport elements extend through the atomizer chamber such that the liquid transport elements are in fluid contact with the aerosol precursor composition contained in the cartridge.

8. The aerosol delivery device of claim 1, wherein the heating elements are configured to be independently controllable.

9. The aerosol delivery device of claim 1, wherein the aerosol channel extends from one end of the reservoir cartridge to the other end of the reservoir cartridge.

10. The aerosol delivery device of claim 1, wherein the atomizer chamber has a substantially half-cylinder shape.

11. The aerosol delivery device of claim 1, wherein the reservoir cartridge comprises at least one reservoir compartment.

12. The aerosol delivery device of claim 11, wherein the at least one reservoir compartment comprises a single reservoir compartment.

13. The aerosol delivery device of claim 11, wherein the at least one reservoir compartment comprises two or more separate reservoir compartments that are sealingly independent from each other.

* * * * *